US007728123B2

(12) United States Patent
Vickery et al.

(10) Patent No.: US 7,728,123 B2
(45) Date of Patent: Jun. 1, 2010

(54) INTERNAL CONTROL NUCLEIC ACID MOLECULE FOR NUCLEIC ACID AMPLIFICATION SYSTEMS

(75) Inventors: Michael C. L. Vickery, Birminham, AL (US); Angelo DePaola, Coden, AL (US); George M. Blackstone, Theodore, AL (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 387 days.

(21) Appl. No.: 11/280,474

(22) Filed: Nov. 15, 2005

(65) Prior Publication Data

US 2006/0166232 A1    Jul. 27, 2006

Related U.S. Application Data

(63) Continuation of application No. PCT/US2004/015175, filed on May 14, 2004.

(60) Provisional application No. 60/471,121, filed on May 16, 2003.

(51) Int. Cl.
C07H 21/04 (2006.01)
(52) U.S. Cl. .................. 536/24.32; 536/24.33
(58) Field of Classification Search ............ 435/6
See application file for complete search history.

(56) References Cited

U.S. PATENT DOCUMENTS

| 5,952,202 | A | 9/1999 | Aoyagi et al. | |
| 6,558,901 | B1 * | 5/2003 | Catanzariti et al. ............ | 435/6 |
| 6,699,703 | B1 * | 3/2004 | Doucette-Stamm et al. ...................... | 435/252.3 |
| 2001/0000148 | A1 | 4/2001 | Kurane et al. | |
| 2001/0000175 | A1 | 4/2001 | Kurane et al. | |
| 2001/0007985 | A1 | 7/2001 | Rothberg et al. | |
| 2001/0024784 | A1 | 9/2001 | Wagner | |
| 2002/0058256 | A1 | 5/2002 | Rothberg et al. | |
| 2002/0102548 | A1 | 8/2002 | Zimmermann et al. | |
| 2002/0106653 | A1 | 8/2002 | Kurane et al. | |
| 2002/0137039 | A1 | 9/2002 | Gessner | |
| 2002/0164613 | A1 | 11/2002 | Villarete et al. | |
| 2002/0168631 | A1 | 11/2002 | Park et al. | |
| 2003/0017482 | A1 | 1/2003 | Godfrey et al. | |
| 2003/0032049 | A1 | 2/2003 | Wagner | |
| 2003/0044826 | A1 | 3/2003 | Ward et al. | |
| 2003/0082582 | A1 | 5/2003 | Gatti | |
| 2003/0082592 | A1 | 5/2003 | Kurane et al. | |
| 2003/0211527 | A1 | 11/2003 | Hartman et al. | |
| 2005/0048475 | A1 * | 3/2005 | Paul et al. ...................... | 435/5 |

FOREIGN PATENT DOCUMENTS

WO    WO 00/29613    5/2000

| WO | WO 01/46463 A2 | 6/2001 |
| WO | WO 02/052030 A2 | 7/2002 |

OTHER PUBLICATIONS

International Search Report mailed Jan. 24, 2005.
Hara-Kudo, Y. et al., "Improved Method for Detection of *Vibrio parahaemolyticus* in Seafood," *Appl. Environ. Microbiol.*, vol. 67, No. 12, pp. 5819-5823 (Dec. 2001).
Hartman, L. et al., "Development of a Novel Internal Positive Control for Taqman® Based Assays," *ASM Abstract Database*, 1 page (Copyright 2003).
Ke, D. et al., "Development of Conventional and Real-Time PCR Assays for the Rapid Detection of Group B Streptococci," *Clinical Chemistry*, vol. 46, No. 3, pp. 324-331 (2000).
Monpoeho, S. et al., "Application of a Real-Time Polymerase Chain Reaction with Internal Positive Control for Detection and Quantification of Enterovirus in Cerebrospinal Fluid," *Eur. J. Clin. Microbiol. Infect. Dis.*, vol. 21, pp. 532-536 (2002).
Myers, M. et al., "PCR Detection of a Newly Emerged Pandemic *Vibrio parahaemolyticus* O3:K6 Pathogen in Pure Cultures and Seeded Waters from the Gulf of Mexico," *Appl. Environ. Microbiol.*, vol. 69, No. 4, pp. 2194-2200 (Apr. 2003).
Rosenstraus, M. et al., "An Internal Control for Routine Diagnostic PCR: Design, Properties, and Effect on Clinical Performance," *J. Clin. Microbiol.*, vol. 36, No. 1, pp. 191-197 (Jan. 1998).
Stöcher, M. et al., "A simple approach to the generation of heterologous competitive internal controls for real-time PCR assays on the LightCycler," *Journal of Clinical Virology*, vol. 25, pp. S47-S53 (2002).
Stöcher, M. et al., "A convenient approach to the generation of multiple internal control DNA for a panel of real-time PCR assays," *Journal of Virological Methods*, vol. 108, pp. 1-8 (2003).
TaqMae® Exogenous Internal Positive Control Reagents VIC™ Probe Protocol, *Applied Biosystems*, pp. i-ii, 1-23 (Copyright 2001).
Vickery, M. et al., "Detection and Quantification of Total and Potentially Virulent *Vibrio parahaemolyticus* Using a 4-Channel Multiplex Real-Time PCR Targeting the *tl*, *tdh*, and *trh* Genes and a Novel PCR Internal Control," *ASM 2003 Annual Meeting, Poster* #Q-082, pp. 1-8 (2003).
Wang, A. et al., "Quantitation of mRNA by the polymerase chain reaction," *Proc. Natl. Acad. Sci. USA*, vol. 86, No. 24, pp. 9717-9721 (Dec. 1989).

(Continued)

*Primary Examiner*—Gary Benzion
*Assistant Examiner*—Cynthia B Wilder
(74) *Attorney, Agent, or Firm*—Merchant and Gould, P.C.

(57) ABSTRACT

The invention provides an internal control nucleic acid molecule including at least one forward primer binding site, at least one reverse primer binding site, and at least one amplifiable region, wherein the forward primer binding site, the reverse primer binding site, and the amplifiable region are all randomly generated. The invention also provides a kit that includes at least one internal control nucleic acid molecule of the invention, at least one forward primer, configured to be complementary to the forward primer binding site of the internal control nucleic acid molecule, and at least one reverse primer, configured to be complementary to the reverse primer binding site of the internal control nucleic acid molecule. The invention also provides methods of using the internal control nucleic acid molecules and kits of the invention.

35 Claims, 23 Drawing Sheets

OTHER PUBLICATIONS

Wellinghausen, N. et al., "Detection of *Legionellae* in Hospital Water Samples by Quantitative Real-Time LightCycler PCR," *Appl. Environ. Microbiol.,* vol. 67, No. 9, pp. 3985-3993 (Sep. 2001).

Zimmermann, K. et al., "Technical Aspects of Quantitative Competitive PCR," *BioTechniques,* vol. 21, No. 2, pp. 268-270, 272, 274-279 (1996).

* cited by examiner

SEQUENCE LISTING

<160> NUMBER OF SEQ ID NOS: 24

<210> SEQ ID NO 1
<211> LENGTH: 19
<212> TYPE: DNA
<213> ORGANISM: Artificial Sequence

```
<220> FEATURE:
<223> OTHER INFORMATION: Forward Primers

<400> SEQUENCE: 1
gacatcgata tgggtgccg                                              19

<210> SEQ ID NO 2
<211> LENGTH: 18
<212> TYPE: DNA
<213> ORGANISM: Artificial Sequence
<220> FEATURE:
<223> OTHER INFORMATION: Forward Primers

<400> SEQUENCE: 2
cgatatgggt gccgttcg                                               18

<210> SEQ ID NO 3
<211> LENGTH: 17
<212> TYPE: DNA
<213> ORGANISM: Artificial Sequence
<220> FEATURE:
<223> OTHER INFORMATION: Forward Primers

<400> SEQUENCE: 3
atgggtgccg ttcgagc                                                17

<210> SEQ ID NO 4
<211> LENGTH: 19
<212> TYPE: DNA
<213> ORGANISM: Artificial Sequence
<220> FEATURE:
<223> OTHER INFORMATION: Reverse Primers

<400> SEQUENCE: 4
gagacgatgc agccattcg                                              19

<210> SEQ ID NO 5
<211> LENGTH: 19
<212> TYPE: DNA
<213> ORGANISM: Artificial Sequence
<220> FEATURE:
<223> OTHER INFORMATION: Reverse Primers

<400> SEQUENCE: 5
cgagacgatg cagccattc                                              19

<210> SEQ ID NO 6
<211> LENGTH: 21
<212> TYPE: DNA
<213> ORGANISM: Artificial Sequence
<220> FEATURE:
<223> OTHER INFORMATION: Reverse Primers

<400> SEQUENCE: 6
aatattcgcg agacgatgca g                                           21

<210> SEQ ID NO 7
<211> LENGTH: 23
<212> TYPE: DNA
<213> ORGANISM: Artificial Sequence
<220> FEATURE:
<223> OTHER INFORMATION: Reverse Primers

<400> SEQUENCE: 7
gagccaagtc agatgatggt acg                                         23
```

```
<210> SEQ ID NO 8
<211> LENGTH: 23
<212> TYPE: DNA
<213> ORGANISM: Artificial Sequence
<220> FEATURE:
<223> OTHER INFORMATION: Reverse Primers

<400> SEQUENCE: 8
gacatgagcc aagtcagatg atg                                             23

<210> SEQ ID NO 9
<211> LENGTH: 252
<212> TYPE: DNA
<213> ORGANISM: Artificial Sequence
<220> FEATURE:
<223> OTHER INFORMATION: Internal Control Nucleic Acid Molecule

<400> SEQUENCE: 9
cgcatgtggt cacagccctg acgaagctgt catcaagttc ataatgacat cgatatgggt      60
gccgttcgag cagtttagcc ctaaatcacc ctaccggcag acgtatgtca cattcaccag     120
ggagacgcat gagattggat gctgttgtgc gccctcaaca atgtaacgaa tggctgcatc     180
gtctcgcgaa tattgtcgta ccatcatctg acttggctca tgtctgcaag aggcttcgca     240
ctgggcttta tg                                                        252

<210> SEQ ID NO 10
<211> LENGTH: 26
<212> TYPE: DNA
<213> ORGANISM: Artificial Sequence
<220> FEATURE:
<223> OTHER INFORMATION: Probe for Internal Control Nucleic Acid
      Molecule

<400> SEQUENCE: 10
tctcatgcgt ctccctggtg aatgtg                                          26

<210> SEQ ID NO 11
<211> LENGTH: 19
<212> TYPE: DNA
<213> ORGANISM: Artificial Sequence
<220> FEATURE:
<223> OTHER INFORMATION: Primers for use with Temperature Limited
      Internal Control

<400> SEQUENCE: 11
tagccctaaa tcaccctac                                                  19

<210> SEQ ID NO 12
<211> LENGTH: 19
<212> TYPE: DNA
<213> ORGANISM: Artificial Sequence
<220> FEATURE:
<223> OTHER INFORMATION: Primers for use with Temperature Limited
      Internal Control

<400> SEQUENCE: 12
agccattcgt tacattgtt                                                  19

<210> SEQ ID NO 13
<211> LENGTH: 17
<212> TYPE: DNA
<213> ORGANISM: Artificial Sequence
<220> FEATURE:
<223> OTHER INFORMATION: Primers for use with Temperature Limited
      Internal Control
```

<400> SEQUENCE: 13
cgagcagttt agccta                                                17

<210> SEQ ID NO 14
<211> LENGTH: 17
<212> TYPE: DNA
<213> ORGANISM: Artificial Sequence
<220> FEATURE:
<223> OTHER INFORMATION: Primers for use with Temperature Limited
      Internal Control

<400> SEQUENCE: 14
ttacattgtt gagggcg                                               17

<210> SEQ ID NO 15
<211> LENGTH: 21
<212> TYPE: DNA
<213> ORGANISM: Artificial Sequence
<220> FEATURE:
<223> OTHER INFORMATION: Primers for use with Temperature Limited
      Internal Control

<400> SEQUENCE: 15
caagttcata atgacatcga t                                          21

<210> SEQ ID NO 16
<211> LENGTH: 19
<212> TYPE: DNA
<213> ORGANISM: Artificial Sequence
<220> FEATURE:
<223> OTHER INFORMATION: Primers for use with Temperature Limited
      Internal Control

<400> SEQUENCE: 16
ccattcgtta cattgttga                                             19

<210> SEQ ID NO 17
<211> LENGTH: 17
<212> TYPE: DNA
<213> ORGANISM: Artificial Sequence
<220> FEATURE:
<223> OTHER INFORMATION: Primers for use with Temperature Limited
      Internal Control

<400> SEQUENCE: 17
ccgttcgagc agtttag                                               17

<210> SEQ ID NO 18
<211> LENGTH: 18
<212> TYPE: DNA
<213> ORGANISM: Artificial Sequence
<220> FEATURE:
<223> OTHER INFORMATION: Primers for use with Temperature Limited
      Internal Control

<400> SEQUENCE: 18
gtacgacaat attcgcga                                              18

<210> SEQ ID NO 19
<211> LENGTH: 20
<212> TYPE: DNA
<213> ORGANISM: Artificial Sequence
<220> FEATURE:
<223> OTHER INFORMATION: Primers for use with Temperature Limited
      Internal Control

```
<400> SEQUENCE: 19
caagttcata atgacatcga                                        20

<210> SEQ ID NO 20
<211> LENGTH: 18
<212> TYPE: DNA
<213> ORGANISM: Artificial Sequence
<220> FEATURE:
<223> OTHER INFORMATION: Primers for use with Temperature Limited
      Internal Control

<400> SEQUENCE: 20
ccattcgtta cattgttg                                          18

<210> SEQ ID NO 21
<211> LENGTH: 18
<212> TYPE: DNA
<213> ORGANISM: Artificial Sequence
<220> FEATURE:
<223> OTHER INFORMATION: Primers for use with Temperature Limited
      Internal Control

<400> SEQUENCE: 21
tagccctaaa tcacccta                                          18

<210> SEQ ID NO 22
<211> LENGTH: 16
<212> TYPE: DNA
<213> ORGANISM: Artificial Sequence
<220> FEATURE:
<223> OTHER INFORMATION: Primers for use with Temperature Limited
      Internal Control

<400> SEQUENCE: 22
gcacaacagc atccaa                                            16

<210> SEQ ID NO 23
<211> LENGTH: 19
<212> TYPE: DNA
<213> ORGANISM: Artificial Sequence
<220> FEATURE:
<223> OTHER INFORMATION: Primers for use with Temperature Limited
      Internal Control

<400> SEQUENCE: 23
tagccctaaa tcaccctac                                         19

<210> SEQ ID NO 24
<211> LENGTH: 17
<212> TYPE: DNA
<213> ORGANISM: Artificial Sequence
<220> FEATURE:
<223> OTHER INFORMATION: Primers for use with Temperature Limited
      Internal Control

<400> SEQUENCE: 24
gcacaacagc atccaat                                           17
```

INTERNAL CONTROL NUCLEIC ACID MOLECULE FOR NUCLEIC ACID AMPLIFICATION SYSTEMS

CROSS-REFERENCE TO RELATED APPLICATIONS

This application is a continuation of and claims priority to PCT/US2004/015175, entitled INTERNAL CONTROL NUCLEIC ACID MOLECULE FOR NUCLEIC ACID AMPLIFICATION SYSTEMS, filed on 14 May 2004 in the name of Michael C. L. Vickery, a U.S. citizen, Angelo Depaola, a U.S. citizen, and George M. Blackstone, a U.S. citizen, applicant/inventor for all designated countries, claiming priority to U.S. Provisional Application No. 60/471,121 filed 16 May 2003.

This application claims priority to U.S. Provisional Application No. 60/471,121, filed on May 16, 2003, entitled INTERNAL CONTROL NUCLEIC ACID MOLECULE FOR REAL-TIME POLYMERASE CHAIN REACTION, the disclosure of which is incorporated by reference herein.

STATEMENT REGARDING FEDERALLY SPONSORED RESEARCH OR DEVELOPMENT

This invention is supported by the Department of Health and Human Services. The Government of the United States of America may have certain rights in the invention disclosed and claimed herein below.

FIELD OF THE INVENTION

The invention relates to amplification methods for nucleic acids. More specifically, the invention relates to an internal control system for use in the amplification of nucleic acid molecules.

BACKGROUND OF THE INVENTION

With the advent of real-time (kinetic) polymerase chain reaction (PCR) analysis, using appropriate standards and sample preparation techniques it is now possible to directly identify the presence of specific nucleic acid sequences and even quantify the number of target nucleic acid molecules in a sample without the need for post-PCR analysis methods, such as gel electrophoresis. Such technology may be useful for identification and/or quantification of specific organisms (e.g. bacteria or other pathogens), identification of specific genes or transcripts, viral detection and quantification, as well as a myriad of other applications. However, one of the risks associated with testing samples by PCR is the occurrence of false negatives.

While a positive and negative control are normally run for every PCR master mix to ensure the integrity of the reagents, inhibition of the PCR by the sample matrix may cause an individual test sample to report a negative result, even if there is target template present in the reaction. In quantitative real-time PCR this is even more of a concern, as partial PCR inhibition may lead to inaccurate quantification results. Therefore, it is desirable to include an internal positive control in each individual reaction to prevent the reporting of false negatives and to potentially allow accurate adjustments to quantitative data.

At present, only a few internal positive control reagents are available commercially. For example, an internal control is available from Applied Biosystems as a component that can be incorporated into TaqMan® (Applied Biosystems) PCR kits and can be spiked into samples to distinguish true target negatives from negatives due to PCR inhibition. The TaqMan® internal positive control sequence can distinguish different types of negative results: (a) a negative call for the target sequence and a positive call for the IPC suggests that no target sequence is present; and (b) a negative call for the target sequence and negative call for the IPC suggests PCR inhibition.

Another example of an internal positive control was reported by Rosenstraus M., et al., (1998) *J. Clinical Microbiol* 36(1):191-197. That group constructed internal control nucleic acids for use in COBAS AMPLICOR tests for *Chlamydia trachomatis, Neisseria gonorrhoeae, Mycobacterium tuberculosis*, and human hepatitis C Virus. The internal control sequence constructed by Rosenstraus et al. had primer binding regions identical to those of the target sequence primers but included a unique probe binding region that differentiated the internal control sequence from amplified target nucleic acid. Because only 20 copies of the internal control sequence were introduced into each test sample, a positive internal control signal indicated that amplification was sufficient to generate a positive signal from targets present at the limit of test sensitivity.

Using the Rosenstraus internal control sequence as a model, Danbing Ke, et al., (2000) *Clinical Chemistry* 46(3): 324-331, constructed an internal control sequence for a PCR assay used to quantify Group B Streptococci. However, this internal control had to be constructed de novo to make it compatible with the Streptococci Group B assay. Using the method of Rosenstraus it was necessary to synthesize the internal control to utilize the same primer binding sequence set as the Streptococci Group B assay used.

A similar limitation is demonstrated in Wellinghausen et al., (2001) *Appl Environ Microbiol.* 67(9):3985-93, which used an internal control that utilizes a known (naturally occurring) lambda phage DNA sequence flanked by assay gene-specific primer regions. This internal control is also designed only for use in a particular assay.

A recent abstract from Hartman et al. (Hartman et al., ASM General Meeting Abstracts, May 2003) also includes similar limitations. Hartman et al. disclosed a Taqman® internal control that has mutated primers and probe binding sites. The assay is designed to amplify the same target DNA, but with different primers and probes. This assay is also specific to the Taqman® assay and would not be universally applicable.

As shown, known methods of providing internal controls have limitations due in large part to the need for sequence customization and reaction specificity. Therefore, there remains a need for an internal control molecule designed as part of a comprehensive internal control system and methods for its use that can be universally incorporated into virtually any PCR assay.

Citation of the above documents is not intended as an admission that any of the foregoing is pertinent prior art. All statements as to the date or representation as to the contents of these documents is based on the information available to the applicant and does not constitute any admission as to the correctness of the dates or content of these documents.

SUMMARY OF THE INVENTION

The invention provides an internal control nucleic acid molecule including at least one forward primer binding site, at least one reverse primer binding site, and at least one amplifiable region, wherein the forward primer binding site, the reverse primer binding site, and the amplifiable region are all randomly generated.

The invention also provides a kit that includes at least one internal control nucleic acid molecule of the invention, at least one forward primer, configured to be complementary to the forward primer binding site of the internal control nucleic acid molecule, and at least one reverse primer, configured to be complementary to the reverse primer binding site of the internal control nucleic acid molecule.

The invention also provides methods of using the internal control nucleic acid molecules and kits of the invention.

DETAILED DESCRIPTION OF THE INVENTION

Figure 1:
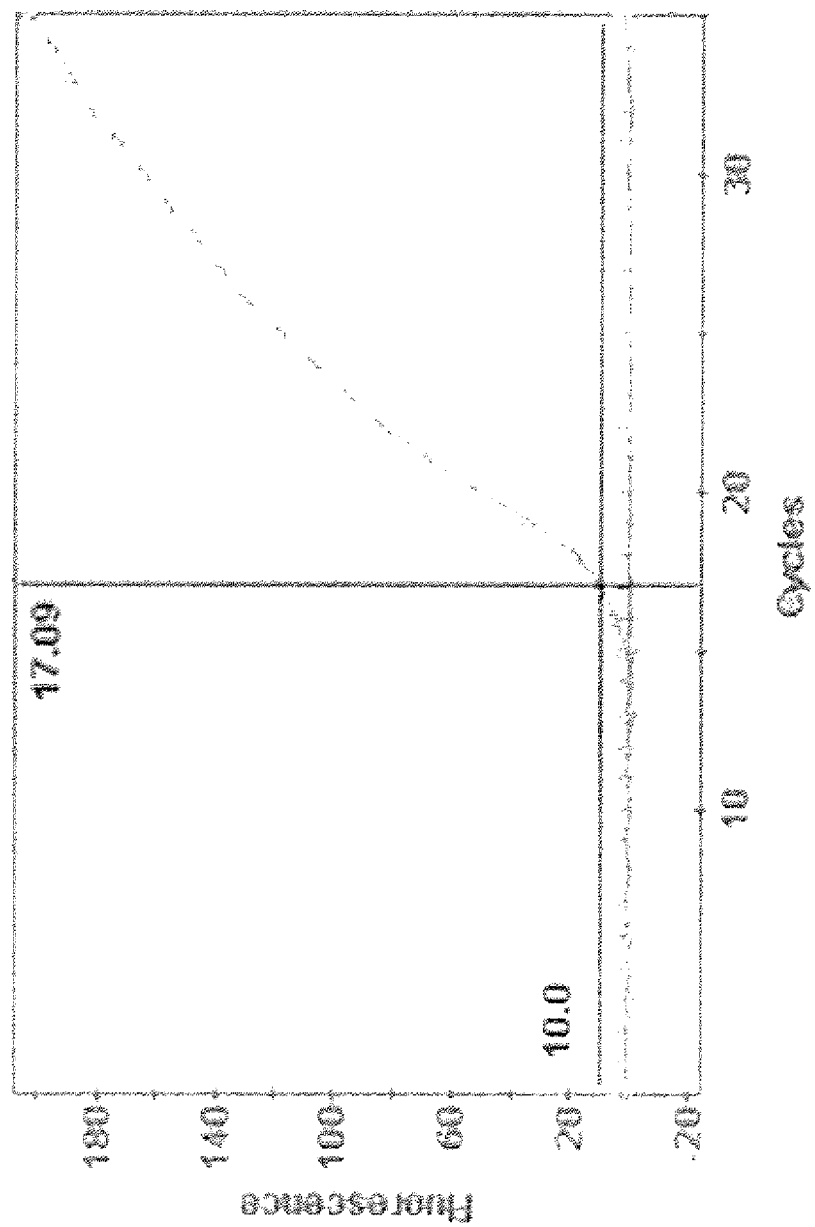
FIG. 1 illustrates a graph of cycles versus fluorescence showing multiplex amplification of thermolabile hemolysin (tl), thermostable direct hemolysin (tdh), and thermostable related hemolysin (trh) (ROX™, FAM™, and TET™ channels respectively).

The invention includes a nucleic acid molecule, which is also referred to herein as an internal control nucleic acid molecule, an internal control molecule, or an internal control.

Internal control nucleic acid molecules in accordance with the invention can function as a part of a system to provide a method of eliminating false negatives during nucleic acid amplification procedures and/or associated detection methods. Examples of nucleic acid amplification procedures where internal control nucleic acid molecules of the invention may be useful include but are not limited to conventional polymerase chain reaction (PCR), real-time polymerase chain reaction (PCR) (also known as qPCR or kinetic PCR), conventional and real-time multiplex PCR assays, conventional and real-time reverse transcription PCR (RT-PCR), nucleic acid sequence based amplification (NASBA), and on-chip PCR amplification on nucleic acid based microarrays. Internal control nucleic acid molecules can also function to provide a means to estimate the degree of PCR inhibition in reactions that make use of the quantitative capabilities of real-time PCR and RT-PCR. If a substance is present in a test sample matrix which inhibits or enhances the PCR amplification, the degree of inhibition or enhancement may be estimated and the quantitative data may be adjusted based upon shifts in the amplification characteristics (for example shifts in the real-time PCR cycle threshold (Ct) value) of the internal control.

In one embodiment of the invention, an internal control nucleic acid molecule can function to provide a method of eliminating false negatives in a real-time multiplex PCR assay. In one embodiment, the real-time multiplex PCR assay may be amplifying and detecting at least three target genes plus the internal control molecule over a range of sensitivity ranging from 1 million copies of each target to one copy of each target nucleic acid sequence. The internal control nucleic acid molecule in accordance with the invention can function by providing a known amplifiable gene for inclusion in a nucleic acid amplification procedure to ensure that the sample conditions are not inhibiting amplification of the nucleic acids. In addition, data obtained during amplification of the internal control may be used to estimate PCR inhibition and adjust quantitative data in quantitative assays.

An internal control nucleic acid molecule in accordance with an embodiment of the invention includes at least one forward primer binding site, at least one reverse primer binding site, and at least one amplifiable region.

In one embodiment of the invention, the forward primer binding site and the reverse primer binding site include from about 15 to about 25 base pairs each. In another embodiment of the invention, the forward primer binding site and the reverse primer binding site include from about 18 to about 24 base pairs each. In yet another embodiment, the forward primer binding site and the reverse primer binding site include from about 20 to about 23 base pairs each.

The amplifiable region is flanked by the forward primer binding site on one end and by the reverse primer binding site on the other end. The length of the amplifiable region, i.e., the region between the forward primer binding site and the reverse primer binding site can vary greatly from as little as about 15 base pairs to greater than about 1000 base pairs. The length of the amplifiable region can depend on a number of factors, including, but not limited to the length of the target genes that the nucleic acid amplification procedure is targeting. In one embodiment of the invention, it may be advantageous to have the length of the amplifiable region different than the length of the target gene of the nucleic acid amplification procedure. In such an embodiment, the difference in length may be desired so that the amplifiable region and the target gene can be confirmed using gel electrophoresis for example. In such an embodiment, it may be desired that the length of the amplifiable region is less than or greater than the length of the target gene(s) by at least about 5 to about 10 base pairs. In another embodiment of the invention, the length of the amplifiable region in relation to the length of the target gene is irrelevant. In another embodiment of the invention the size of the amplifiable region is desired to be close to that of the assay target sequence in order that the internal control will have amplification characteristics similar to those of the target sequences(s).

The forward primer binding site, the reverse primer binding site, and the amplifiable region are all pseudo-randomly generated. The phrase "pseudo-randomly generated" means that the sequences are randomly generated with certain design characteristics being taken into consideration. The sequence of base pairs of the forward primer binding site, the reverse primer binding site, and the amplifiable region can be determined by any method know to those of skill in the art for determining a random sequence of four possibilities (A, T, G, and C). Examples of such methods, include but are not limited to, use of computer software designed to produce random nucleotide sequences.

There are a number of design characteristics that can be considered when generating the sequences. Examples of these considerations include, but are not limited to: the GC content of the sequence; a lack of identity to any known, naturally occurring sequences, or PCR-amplifiable region; and the lack of repetitive regions of the same base pair. The pseudo-randomly generated sequence can be designed by considering any combination of these various characteristics.

One design characteristic that can be utilized to pseudo-randomly generated an internal control molecule is the GC content of the sequence. In one embodiment, the GC content of the internal control molecule, or a portion thereof can be specified to be within a certain range. It may be advantageous to specify a particular GC content or a range of a GC content in order to mimic the GC content, or the typical GC content range of a specific organism or target gene. This would allow the internal control molecule to be more specifically tailored to mimic nucleic acid amplification properties of an organism or gene. In one embodiment, the GC content of the internal control molecule can be specified to be between about 20% to about 80% GC for example.

It may be desirable to consider the GC content of the internal control molecule because the GC content of a nucleic acid sequence can be a factor in the amplification behavior of that sequence. Therefore, it may be advantageous to mimic the GC content of a nucleic acid sequence in order to more closely mimic the amplification behavior of that sequence within a given amplification method. Alternatively, the GC content of an internal control molecule may be chosen based on the particular method of amplification.

In one embodiment of the invention, the sequences of the forward primer binding site, the reverse primer binding site, and the amplifiable region have a low GC content. As used herein, the phrase "low GC content" refers to a sequence that has significantly less than the approximate average GC content of a typical prokaryotic or eukaryotic gene. In another embodiment, the sequences of the forward primer binding site, the reverse primer binding site, and the amplifiable region have a high GC content. As used herein, the phrase "high GC content" refers to a sequence that has significantly more than the approximate average GC content of a typical prokaryotic or eukaryotic gene.

It may also be advantageous to have an internal control molecule that includes at least one region of high GC content and at least one region of low GC content. Such an embodiment of an internal control molecule may be useful in a number of different methods of amplification for a number of different types of organisms.

Another design characteristic that can be taken into consideration is that the internal control sequence has no significant nucleotide identity to any known, naturally occurring nucleotide sequences. As used herein, the phrase "no identity to any known, naturally occurring nucleotide sequences" means that the sequence of base pairs of the forward primer binding site and the reverse primer binding site are designed such that they should not hybridize to naturally-occurring nucleotide sequences in a PCR-amplifiable region of the genome of a single organism. Thus the randomly generated primers should in combination (forward and reverse) not typically be capable of amplification of a naturally-occurring sequence at the hybridization temperatures and polymerase extension times typically used in real-time PCR.

Yet another design characteristic that can be considered is that the amplifiable region itself has no significant identity to any known, naturally occurring amplifiable region of a nucleotide sequence. As used herein, the phrase "no significant identity to any known, naturally occurring PCR-amplifiable region of a nucleotide sequence" means that the amplifiable region does not have the same base pair sequence of any known, naturally occurring region or a known naturally occurring nucleotide sequence that is able to be amplified by nucleotide amplification procedures. In one embodiment, the forward and reverse primers may separately have accidental sequence identity to some small part of the genome of some organism. Using very short primers the chances of finding some identity to an organism can be great, but using primers of the length specified for these internal controls, i.e. from about 15 to about 25 base pairs, the chances are significantly reduced.

However, using pseudo-randomly generated sequences in accordance with an embodiment of the invention, the primers are statistically highly unlikely to bind to adjacent nucleotide sequence that are amplifiable in a single organism—especially in the organism that is being assayed, at the temperatures typically used for most real time PCR assays.

A further design characteristic that can be considered is that the internal control sequence is free of repetitive regions of the same base pair. In one embodiment, the sequences of the forward primer binding site, the reverse primer binding site, and the amplifiable region do not have a string of more than four (4) bases that are the same in the sequence. In another embodiment of the invention, the sequences of the forward primer binding site, the reverse primer binding site, and the amplifiable region do not have a string of more than five (5) bases that are the same in the sequence.

Yet another design characteristic that can be considered is the secondary structure of the sequence. In one embodiment it is desired to have no or little secondary structure present in the internal control molecule. In another embodiment, it is desired to have an internal control molecule that has secondary structure. Secondary structure can alter the amplification behavior of a nucleic acid sequence, therefore, it may be advantageous to consider the secondary structure of the internal control molecule in an effort to mimic the amplification behavior of the nucleic acid sequence to be amplified.

In one embodiment of the invention, internal control nucleic acid molecules can be "tailored" to a specific organism or assay. By "tailored" it is meant that the internal control nucleic acid molecule can be designed in order to mimic certain design characteristics of the nucleic acid molecules already present in the organism. In one embodiment, the nucleic acid molecule already present in the organism is the target of the assay. In another embodiment of the invention, the internal control nucleic acid molecule can be "tailored" to the particular assay that is being used. In this embodiment, the sequence would be generated in an effort to take into consideration certain amplification behaviors of the assay. In yet another embodiment, the internal control nucleic acid molecule can be designed without tailoring, or with limited tailoring of the sequence to either the target gene or the amplification method to be used. In one embodiment, the "tailoring" that could be done would include accounting for the GC content and secondary structure (or lack thereof) of the target gene.

In yet another embodiment, the invention provides an internal control nucleic acid molecule, or a kit containing such an internal control molecule, that can be utilized, without modification of either the internal control molecule or the assay method, in virtually any assay for virtually any target gene without further modification, or tailoring, as is referred to above.

Exemplary sequences of reverse primers, which could be utilized to create the complementary reverse primer binding sites include, but are not limited to the following sequences.

```
gacatcgata tgggtgccg      SEQ ID NO:1 cgatatgggt gccgttcg       SEQ ID NO:2 atgggtgccg ttcgagc        SEQ ID NO:3
```

Exemplary sequences of forward primers, which could be utilized to create the complementary forward primer binding sites include, but are not limited to the following sequences.

```
gagacgatgc agccattcg      SEQ ID NO:4 cgagacgatg cagccattc      SEQ ID NO:5 aatattcgcg agacgatgca g   SEQ ID NO:6 gagccaagtc agatgatggt acg SEQ ID NO:7 gacatgagcc aagtcagatg atg SEQ ID NO:8
```

In one embodiment of the invention, a sequence that is pseudo-randomly generated is generated by taking into consideration a desired GC content, or a desired range of GC content and then editing the sequence to remove any secondary structure present in the internal control molecule.

In one embodiment, an internal control nucleic acid of approximately 250 base pairs can be designed using the following procedure. Ten random sequences of about 50 bases are generated using a random sequence generator (using the average natural GC and AT base pair content of prokaryotic and eukaryotic organisms as a guideline) to generate a series of the bases adenine (A), cytosine (C), guanine (G), and thymine (T). These sequences can be checked against the GenBank to ensure that they do not significantly match any known naturally occurring amplifiable regions of nucleic acids. Any sequences which fail to meet the designated criteria are thrown out and new ones are generated. The random sequences are then chained together to create an approximately 500 base pair sequence. Then, a software program, such as DNASTAR's Lasergene MegAlign™ (DNASTAR, Madison, Wis.) can be utilized to determine if there is any significant secondary structure, which might inhibit primer or probe binding, or repetitive regions in the overall sequence. If there is significant secondary structure, these regions are edited out or the process is begun again and the 50 base pair sequences can be recombined differently to attempt to remove the secondary structure. The size of the final nucleic acid molecule is then edited to the desired length. The nucleic acid sequence generated by the method above can be much larger (thousands of base pairs) or much smaller (<100 base pairs) if desired.

The above exemplary procedure represents only one method of designing an internal control nucleic acid molecule in accordance with the invention. The pseudo-random sequence of the internal control nucleic acid molecule may be designed using any number of similar methods and/or various software packages with the same result. It will be understood by one of skill in the art, having read this specification, that any method of carrying out steps similar to the above can be utilized to design an internal control nucleic acid molecule in accordance with the invention.

Internal control nucleic acid molecules can include deoxyribonucleic acid (DNA), and ribonucleic acid (RNA).

One of skill in the art will also understand that once the internal control nucleic acid molecule has been designed, it can be made by any method commonly known and used by those of skill in the art. Alternatively, the internal control nucleotide molecule can be synthesized by a company such as Integrated DNA Technologies (Coralville, Iowa). It is also practical to synthesize this molecule in most molecular biology laboratories by combining specific synthesized oligonucleotides into a designated sequence.

In another embodiment of the invention, the internal control nucleic acid molecule also includes at least one probe binding region. The probe binding region can be configured to be complementary to a real-time PCR probe. The probe for which the probe binding region is complementary may be any probe that is commonly known and used in assays for DNA detection and/or quantification. The nucleotide sequence of the probe is designed to be complementary to a region of the internal control nucleic acid molecule of the invention that can be amplified by PCR using primers designed for use with the internal control nucleic acid molecule as previously described. If for example, probe A with a base pair sequence of ATCTCG is going to be used, the probe binding region would have a sequence of (for example) CGAGAT. The probe can be designed using specifications unique to each type of probe—typically using specialized software such as (for example) Primer Express (Applied Biosystems, Foster City, Calif.). The probe will behave much like a primer in terms of the hybridization of the probe to the internal control DNA sequence in that it is designed to hybridize to regions in the internal control nucleic acid molecule. These regions are unlikely to have nucleotide identity to regions internal to amplifiable regions in any naturally-occurring sequences for the same reasons described above for the primer binding regions.

The primers and probes used with the internal control nucleic acid molecule can be designed with characteristics specific to certain types of real-time PCR assays (or conventional PCR assays) and can be designed using computer software such as Primer Express. Examples of these characteristics include, but are not limited to amplicon size and primer melting temperature. The primers and probes are designed to be compatible during amplification without the formation of primer dimers. If primer dimmers form as a result of cross-hybridization with existing assay primers, alternative internal control primers may be utilized to prevent the formation of primer diners such that the internal control sequence may be utilized with any existing conventional or real-time PCR assay without the formation of primer dimers. The primers and probes are chosen to be complementary to amplifiable regions of the internal control DNA molecule.

Examples of assays that may utilize a probe include, but are not limited to the 5' nuclease assay, which is known commercially as Taqman ® (Applied Biosystems). In the Taqman® assay, a probe can be utilized that is designed to bind to a DNA sequence internal to the primers targeting a specific amplification region. The probe is typically labeled at the 5' end with a reporter molecule such as a fluorescent dye and a quencher molecule at the 3' end. Specific examples of exemplary probes that can be utilized in combination with the probe binding region of an internal control nucleic acid molecule of the invention include, but are not limited to, a 5' nuclease type probe, a TaqMan® MGB (minor groove binder) probe (which can be synthesized by Applied Biosystems), a Scorpion® probe, a lightcycler style "FRET" probe set, an Eclipse probe, a molecular beacon, and numerous others. Examples of types of fluorophores and the respective quenchers that the probes can be labeled with include, but are not limited to, sulfarhodamine (TX-Red®) or 6-carboxy-X—

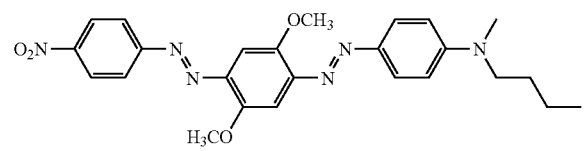

rhodamine (ROX™) and Black Hole Quencher™-2) (which can be synthesized by Integrated DNA Technologies), 6-carboxyfluoresceint (FAM™), tetrachloro-6-carboxy-fluorescein (TET™), 2'-chloro-7'-phenyl-1,4-dichloro-6-carboxyfluorescein (VIC™), and cyanine dyes, such as cyanine 3 (Cy3®) and cyanine 5 (Cy5®), and numerous other dyes combined with various non-fluorescent or fluorescent quencher dyes.

The internal control nucleic acid molecule and internal control system may also be utilized in assays that use intercalating dyes such as Sybr® Green (Molecular Probes) to report amplification of nucleic acid sequences. Through the use of melt curve analysis the amplified internal control nucleic acid molecule may be identified and distinguished from the assay target amplicons in an amplification reaction that includes such intercalating dyes.

The internal control nucleic acid molecule and internal control system may be utilized in multiplex conventional or real-time PCR or RT-PCR assays that simultaneously target multiple genes or RNA transcripts.

One embodiment of the invention is a kit that includes an internal control nucleic acid molecule of the invention in combination with at least one primer molecule. Another embodiment of the invention is a kit that includes an internal control nucleic acid molecule of the invention in combination with a set of primer molecules. The primer set can be composed of a forward and a reverse primer complementary to a forward primer binding site and a reverse primer binding site of the internal control nucleic acid molecule. In one embodiment, the kit contains at least one primer set. In another embodiment, the at least one primer set itself can be fluorescently labeled with fluorescent reporter molecules (offered by Invitrogen, Carlsbad, Calif., and other companies). The internal control nucleic acid molecule included in the kit may also have at least one probe binding site. In such an embodiment, the kit may, but need not include at least one probe. The internal control nucleic acid molecule may be supplied at a concentration such that it can be diluted to a level to provide optimum performance for a given reaction.

In one embodiment of the invention, an internal control nucleic acid molecule of the invention (either in a kit or not) can include more than one forward primer binding site and more than one reverse primer binding site. In such an embodiment, the portion of the amplified region that actually gets amplified when the internal control nucleic acid molecule is subject to PCR amplification depends on the specific primer pair (i.e., reverse and forward primers) that is added to the PCR reaction mixture. For example, if a primer pair (a specific forward and specific reverse primer) is added to the PCR reaction mixture before amplification, the region between the complementary forward primer binding site and the reverse primer binding site will be amplified.

In an embodiment where the internal control nucleic acid molecule contains more than one forward primer binding site and more than one reverse primer binding site, the specific forward primer binding sites and reverse primer binding sites that are included can be chosen based on a number of factors. One consideration when designing various forward and reverse primer binding sites can include the temperature at which the complementary primers anneal. It may be desirable to include various sets of forward and reverse primer binding regions that have complementary forward and reverse primers that anneal over a wide array of temperatures to match the requirements of individual assays without changing the assay temperature cycling conditions in PCR applications. This would allow a user to choose an internal control nucleic acid molecule amplicon that would be amplified before the target gene (i.e., at a lower anneal temperature), at the same time as the target gene (i.e., at about the same temperature), or after the target gene (i.e, at a lower anneal temperature).

Generally, primers have melting temperatures of about 55° C. to about 70° C., but may have melting temperatures as low as 37° C. and as high as 72° C. Using primers designed with melting temperatures lower than the meting temperatures of the assay targets, the internal control system may be utilized for temperature-limited cycling protocols in which the internal control nucleic acid sequence is amplified at a temperature lower than the assay target sequences, with the reaction temperature then being raised to a higher assay temperature once amplification of the internal control has been detected. Once the temperature of the assay is raised, amplification of the internal control molecule is reduced or eliminated in order to prevent competition of the internal control reagents with the assay primers. The specific primers can also be chosen based on the desired size of the amplifiable region to make the internal control system capable of incorporation into any assay at a size desired by the user.

Another embodiment of the invention includes a method of monitoring for false-negative detections in real time PCR that includes adding at least one internal control nucleic acid molecule in accordance with the invention to a real-time PCR reaction mixture that includes a sample, where the internal control nucleic acid molecule includes at least one forward primer binding site, at least one reverse primer binding site, an amplifiable region, and a probe binding site; adding at least one forward primer and at least one reverse primer that are complementary to at least one forward primer binding site and at least one reverse binding site in the internal control nucleic acid molecule, wherein said forward and reverse primers are suitable to specifically amplify the amplifiable region of the internal control nucleic acid molecule; adding at least one probe, wherein said probe is hybridizable to said probe binding site; amplifying said amplifiable region to create amplicons of said internal control nucleic acid molecule; and detecting the presence of said amplicons, wherein the detection of said amplicons prevent false-negative results for amplification of a target sequence performed by said real-time PCR. Another embodiment of the invention includes a method of monitoring for PCR inhibition or enhancement in quantitative real-time PCR using the internal control system described herein. Shifts in the CT value of the internal control may be used to adjust real-time PCR quantitative data using appropriate standards and controls, allowing for more accurate quantification from samples containing substances that may inhibit or enhance PCR.

The method of the invention can be carried out in combination with any known method for quantitative real-time PCR. One of skill in the art, having read this specification, would understand how to incorporate an internal control nucleic acid molecule in accordance with the invention into a quantitative real-time PCR method.

An internal control nucleic acid molecule in accordance with the invention can be universally adapted to any assay or instrument platform. In addition, the invention allows one to choose multiple primer sets to ensure compatibility with the assay primer sets and amplicon sizes.

It is also an additional advantage of the invention that an internal control molecule of the invention does not compete with amplification of the target molecule, as do other internal control molecules that have been used in the prior art. This is not a concern when using an internal control nucleic acid molecule of the invention since the primers of the internal control are distinct from the target primers, and because of the design of the internal control molecule, are unlikely to amplify naturally occurring sequences. As such, inclusion of an internal control nucleic acid molecule of the invention minimizes interference either with the quantitative abilities or the sensitivity (down to a single cell) of a triplex assay (3 targets) as evidenced by the example below.

In one embodiment of the invention, an internal control nucleic acid molecule can be designed to give rise to PCR amplicons of sizes of a range such that an amplicon could be chosen that would be easily distinguished from the target molecule amplicons using agarose gel electrophoresis (e.g., under 500 bases for most real-time PCR assays). For real-time PCR, however, the disparity in sizes of the amplicon internal control molecule and the target may be less important to some users.

In one embodiment of the invention an internal control molecule may be designed to include multiple primer binding sites for forward and reverse primers of multiple annealing temperatures with amplicons of numerous sizes that can be chosen, as well as multiple binding sites for various types of real-time probes, such that a single comprehensive system can be utilized for amplification of an internal control molecule in any type of PCR assay—conventional or real-time, for detection or for quantification, with various thermal cycling schemes available using primers of various annealing temperatures in single or multiplex reactions. This system may be offered as a kit in various configurations as a universal exogenous internal control system for use with virtually any PCR assay for detection or quantification of a target nucleic acid (and related organism). The system may be used in a conventional PCR assay by not including an internal control probe in the reaction. However, in this case, amplification or non-amplification would have to be verified by a post-PCR method such as gel eletrophoresis.

In one embodiment of the invention a kit includes an internal control nucleic acid molecule provided as a linearized plasmid DNA molecule.

In another embodiment of the invention, a kit can include an internal control nucleic acid molecule provided as a circular plasmid DNA molecule.

A further embodiment of the invention is a kit that can include an internal control nucleic acid molecule provided as a double stranded linearized DNA molecule.

A further embodiment of the invention is a kit that includes an internal control nucleic acid molecule provided as a single stranded RNA molecule for use in RT-PCR.

Through the use of a kit of the invention, an internal control molecule in accordance with the invention can easily be incorporated into existing conventional and real-time PCR assays by one of skill in the art, having read this specification.

Having now generally described the invention, the same will be more readily understood through reference to the following examples, which are provided by way of illustration, and are not intended to be limiting of the present invention, unless specified.

EXAMPLE 1

Quantitation of *Vibrio parahaemolyticus* in a Sample

*Vibrio parahaemolyticus* (Vp) is an estuarine bacterium that is the leading cause of shellfish-associated cases of bacterial gastroenteritis in the U.S., with most infections occurring from the consumption of raw or mishandled seafood. Previous methods for the detection of Vp have involved labor and resource intensive testing of individual isolates by various phenotypic assays (Myers, M L et al., Appl Environ Microbiol. 2003 69(4):2194-200; Hara-Kudo, Y. et al., Appl Environ Microbiol. 2001 December; 67(12):5819-23.)The tl (thermolabile hemolysin) gene is a species-specific marker for Vp, while the tdh (thermostable direct hemolysin) and trh (thermostable-related hemolysin) genes are two pathogenicity markers for Vp. There are multiple variants of tdh, all of which are potentially capable of sufficient TDH production to cause illness. Promoter efficiency-related, tdh1 and tdh2 gene variants have been associated with K+ strains. tdh2 causes hemolytic activity in K+ strains. tdh is also found in *V. hollisae, V. fluvialis, V. mimicus, V. cholerae*, and other pathogenic microbes. trh associated with virulence is often present in association with tdh in pathogenic strains. There are also several trh variants—trh1, trh2, and others, which have greater than 84% nucleotide identity. trh has about 70% nucleotide identity with tdh. tdh and trh are in close proximity on the chromosome in tdh+trh+ strains. While tl is a Vp-specific marker, it has significant similarity to tdh and trh in some regions of the gene. A 4-channel real-time multiplex PCR assay was developed using the Smart Cyclers system (Cepheid, Sunnyvale, Calif.). This assay included an internal control nucleic acid molecule of the invention and was designed to optimize the assay for the simultaneous enumeration of total and pathogenic Vp in natural (unenriched) samples.

Internal Control Nucleic Acid Molecule

An exogenous internal control nucleic acid molecules in accordance with the invention was incorporated into this assay. The full-length sequence of the exemplary internal control nucleic acid molecule utilized in this assay is shown below:

```
                                                  SEQ ID NO:9
cgcatgtggt cacagccctg acgaagctgt catcaagttc ataatgacat cgatatgggt   60
gccgttcgag cagtttagcc ctaaatcacc ctaccggcag acgtatgtca cattcaccag  120
ggagacgcat gagattggat gctgttgtgc gccctcaaca atgtaacgaa tggctgcatc  180
gtctcgcgaa tattgtcgta ccatcatctg acttggctca tgtctgcaag aggcttcgca  240 ctgggctttatg                                                       252
```

The probe to hybridize with the nucleic acid molecule is shown in SEQ ID NO:2 below.

tctcatgcgt ctccctggtg aatgtg

SEQ ID NO:10

The internal control was set to report amplification at ~20 PCR cycles when testing either living or boiled cells of pure Vp cultures in APW or phosphate-buffered saline (PBS), which were both shown to not inhibit the reaction.

A person of ordinary skill in the art would be able to synthesize other nucleic acid molecules for use as internal positive controls which include forward and reverse primer binding sites, and probe binding sites that have no identity to any naturally occurring sequence without undue experimentation.

Bacterial Cultures and Genomic DNA Preparation

Selected *V. parahaemolyticus* (Vp) strains (FIHES98, TX2103, AQ4037, and 91A-4950) used for real-time PCR bacterial enumeration experiments were grown for 6 hours at 35° C. in 5 mL alkaline peptone water (APW) (1.0% peptone, 1.0% NaCl, pH 8.5 ± 0.2). Crude cell lysates were prepared from 1 mL aliquots of each of these cultures by boiling for 15 minutes in 1.5 mL microcentrifuge tubes. The genomic DNA contained in these lysates was later used as a template in the real-time PCR assay. Overnight plate counts from T1N3 plates (1.0% tryptone, 3.0% NaCl, 2.0% agar) containing spread dilutions of each 6-hour culture were used to determine the original cfu/mL for each preparation of boiled template. All additional *Vibrio* strains utilized were grown overnight at 35° C. in APW, while all other bacterial strains were grown overnight at 35° C. in Tryptic Soy Broth (1.7% Pancreatic Digest of Casein, 0.3% Enzymatic Soy Digest, 0.25% Dextrose, 0.5% NaCl, 2.5 g/L $K_2HPO_4$, pH 7.3±0.2). Purified genomic DNA was prepared from many strains using the MagNA Pure LC robotic DNA extraction instrument (Roche, Indianapolis, Ind.). A Bacterial DNA Isolation Kit (III) was used for the extraction process, which produced 100 μl of eluted DNA sample from 100 μl of enrichment culture. The purity and concentration of each DNA sample was determined by UV spectrophotometry and fluorometry with PicoGreen® (Molecular Probes, Inc., Eugene, Oreg.), respectively.

Design of Primers and Fluorogenic Probes for Real-time PCR

The complete nucleotide sequences (open reading frame regions only) for all reported variants of the tl, tdh and trh genes of Vp were aligned and compared using Lasergene MegAlign™ software (clustal alignment, PAM250 distance tables) from DNASTAR (Madison, Wis.). An additional unpublished variant of the trh gene (manuscript in preparation) was also included in the alignments. Primer Express Software from Applied Biosystems (Foster City, Calif.) was used to design oligonucleotide primers and TaqMan® or TaqMan® MGB fluorogenic probes targeting regions identified by the alignments as unique to each of these genes. Multiple primer sets were designed and tested for specificity and compatibility in multiplex. Information on the primers and probes utilized in the assay can be seen in Table 1 below.

TABLE 1

| Target | Primers[1]/Probe | Amplicon Size (bp) | Probe Type | Probe Fluorophore | Probe Quencher |
|---|---|---|---|---|---|
| tl gene | tl-F, tl-R/tl-P | 207 | 5'-nuclease[2] | TX-Red ® or Rox ™[4] | Black Hole Quencher ™-2 |
| tdh gene | tdh-F, tdh-R/ tdh-P | 233 | TaqMan MGB[3] | Fam ™ | Non-fluorescent Quencher |
| trh gene | trh-F, trh-R/ trh-P | 273 | TaqMan ® MGB[3] | Tet ™ | Non-fluorescent Quencher |
| Internal Control | IC 46F, IC 186R | 141 bp | 5'-nuclease[2] | Cy-5 ® | Black Hole Quencher ™-2 |

[1]All primers were synthesized by either Integrated DNA Technologies (Coralville, IA) or Invitrogen (Carlsbad, CA).
[2]Synthesized by Integrated DNA Technologies
[3]Synthesized by Applied Biosystems (Foster City, CA), MGB = minor groove binder.
[4]Both fluorophores have been utilized for this assay, using the ROX channel of the original SMART Cycler ® and the TX-Red ® channel of the SMART Cycler ® II.

Real-time PCR Amplification

The real-time PCR cycling protocol, fluorescent detection parameters, and reaction component concentrations were carefully optimized for the simultaneous detection and quantification of the tl, tdh, and trh genes of Vp. PCR was conducted in a 25 μl volume using the following reaction components (final concentrations shown): 1× PCR Amplification Buffer [10× buffer consisted 200 mM Tris-HCl (pH 8.4) and 500 mM KCl] (Invitrogen), 5 mM MgCl2, 400 nM of each of the dNTPs (Roche, Indianapolis, Ind.), 200 nM of each primer (described above), 150 nM of each of the 4 fluorogenic probes (tl, tdh, trh, and internal control), and 2.25 U Platinum™ Taq polymerase (Invitrogen). The remainder of the reaction volume consisted of PCR-grade H2O, Vp target DNA template (either 2 ul of boiled cells or 5 ng of purified DNA), and the internal control reagents. Real time PCR thermal cycling was conducted using the Smart Cycler® II system from Cepheid (Sunnyvale, Calif.). The two-step touchdown cycling parameters utilized are shown below Cycling Parameters 95° C. for 60 s×1 cycle—Denaturation/taq activation 95° C. for 5 s, 64° C. for 45 s×1 cycle—Touchdown
    95° C. for 5 s, 63° C. for 45 s×1 cycle—Touchdown
    95° C. for 5 s, 62° C. for 45 s×1 cycle—Touchdown
    95° C. for 5 s, 61° C. for 45 s×1 cycle—Touchdown
    95° C. for 5 s, 60° C. for 45 s×1 cycle—Touchdown
    95° C. for 5 s, 59° C. for 45 s×40 cycles—Amplification The Smart Cycler® II instrument was programmed to measure the accumulated fluorescence in each reaction tube at the end of each amplification cycle using the FTTC-25 dye calibration set and the default software parameters, except that the Manual Threshold Fluorescent Units setting was changed to 8.0 units above background. A sample was therefore considered to be positive when a signal of at least 8 fluorescence units above baseline (after background correction) was observed in the Fam™, Tet™, TX-Red®, or Cy-5 ® channels of the instrument within 45 cycles. Positive controls of Vp strains possessing all 3 target genes plus the internal control and a negative control (sterile dH2O added as template in the reaction) were prepared for each PCR master mix. For each reaction, a plot of the cycle threshold vs. log fluorescence in the Fam™, Tet™, TX-Red®, or Cy5 ® channels of the Smart Cycler® instrument was examined. Reactions lacking the internal control probe were also performed on a SMART Cycler® SC (the first version of the instrument) using the Fam™, Tet™, and Rox™ channels (tdh, trh, and tl detection, respectively).

Generation of Standard Curves

For determination of the assay sensitivity, dynamic range, and quantitative capabilities, *V. parahaemolyticus* (Vp) strain 91A-4950 (tl, tdh, and trh positive) was used to generate standard curves for each target during multiplex real-time PCR amplification. Dilutions ($10^{-1}$ to $10^{-7}$) in PBS (137 mM NaCl, 2.7 mM KCl, 4.3 mM $Na_2HPO_4 \cdot 7H_2O$, 1.4 mM $KH_2PO_4$, pH 7.3±0.2) were prepared from boiled cells from 6 h cultures with known cfu/ml values (see above). The assay was run in duplicate for each dilution, using 2 μl of template per reaction.

Specificity and Enrichment Testing

Figure 5:
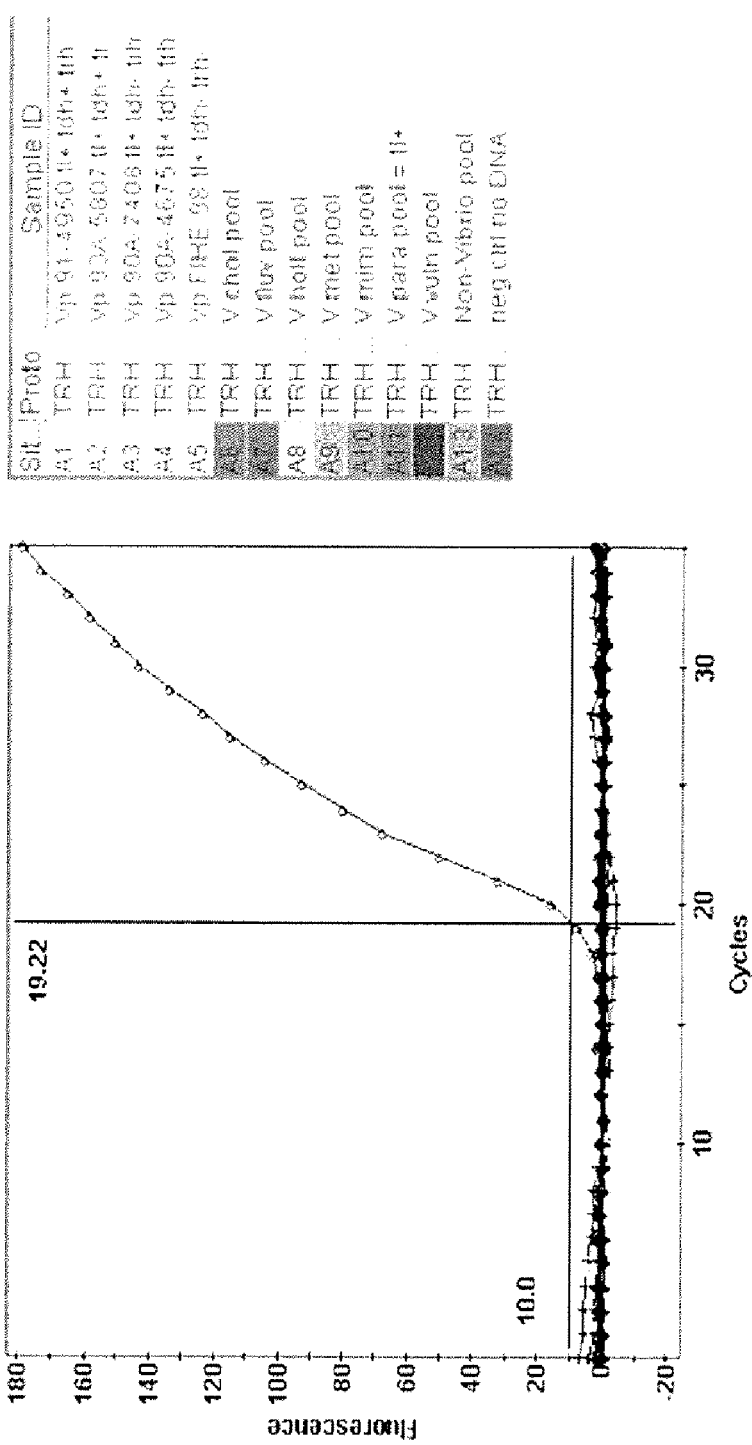
FIG. 5 illustrates a graph of cycles versus fluorescence showing amplification of tl, tdh, and trh against a panel of diverse bacterial isolates (boiled cells).

Using boiled cells and/or purified DNA, the assay was tested for specificity against a panel of >100 bacterial isolates including: *Escherichia coli, Vibrio alginolyticus, V. cholerae, V. fluvialis, V. hollisae, V. metschnikovii, V. mimicus, V. parahaemolyticus, V. vulnificus, Listeria monocytogenes, L. innocua, L. ivanovii, L. seeligeri, L. welshimeri,* and *Salmonella* sp. (FIG. 5). The robustness of the assay was evaluated using enrichments of Vp-spiked oyster homogenate (FIG. 12), oyster mantle fluid (FIG. 13), and shrimp homogenate (FIG. 14). Typically, Vp-spiked samples were blended for 90 s with 9× their weight of APW and incubated overnight at 35° C. before testing. Results The internal control nucleic acid molecule in accordance with the invention showed robust simultaneous detection and quantification of total (tl+) and potentially pathogenic (tdh+ or trh+) strains of Vp.

Figure 2:
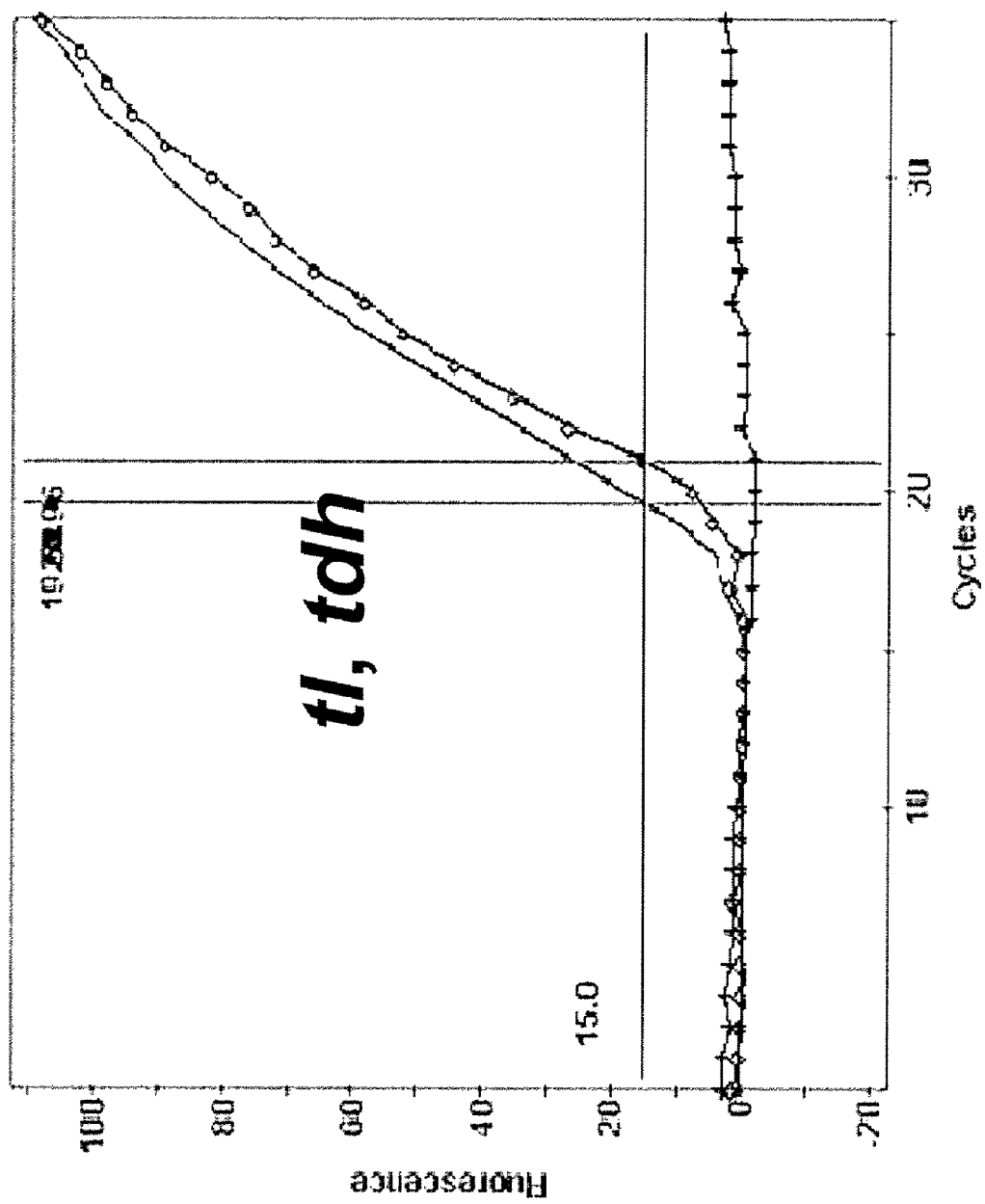
FIG. 2 illustrates a graph of cycles versus fluorescence showing multiplex amplification of tl, tdh, and trh from a *Vibrio parahaemolyticus* (Vp) strain (tl+) possessing the tdh gene but lacking the trh gene (tdh+,trh−).
Figure 3:
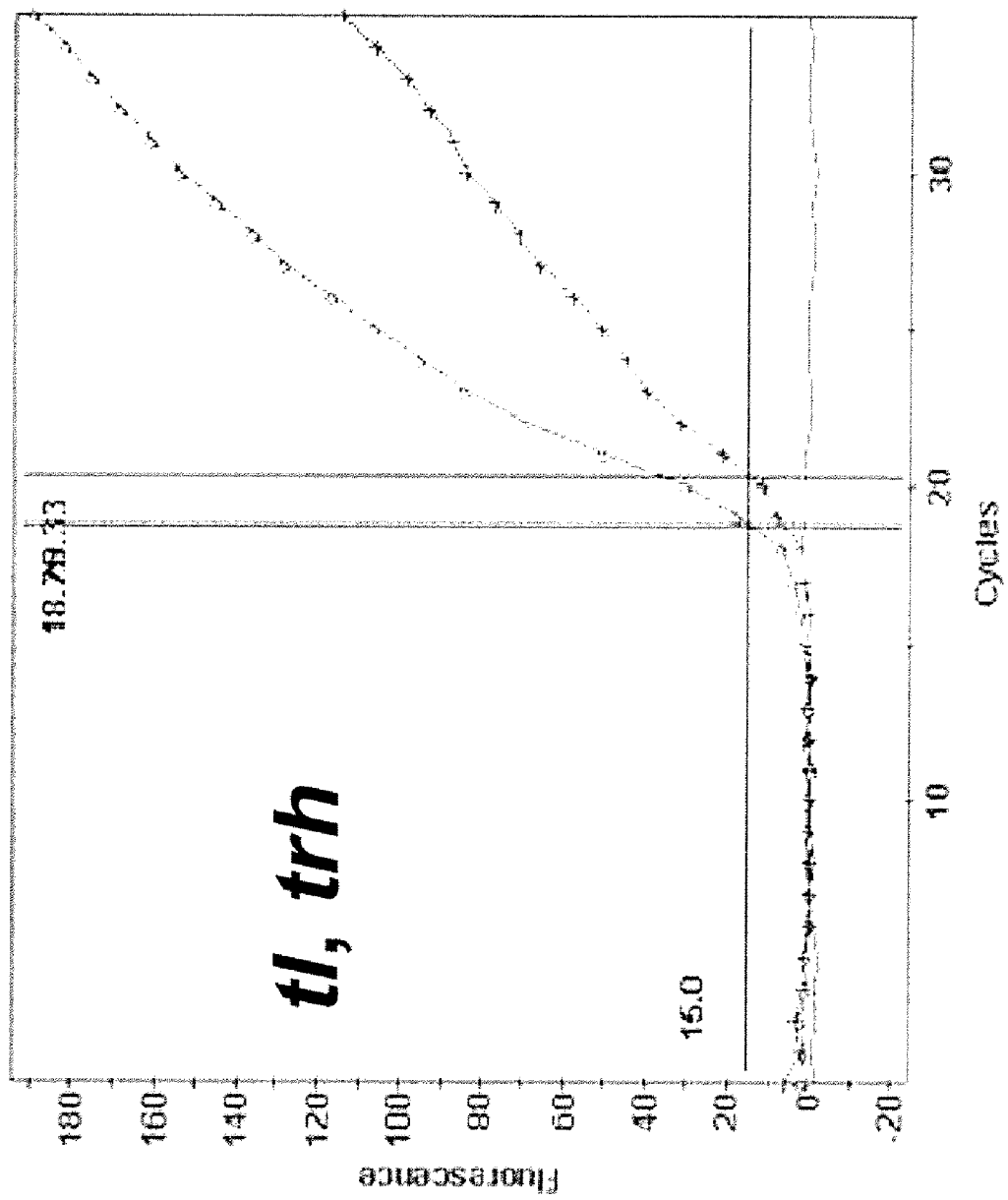
FIG. 3 illustrates a graph of cycles versus fluorescence showing multiplex amplification of tl, tdh, and trh from a Vp strain (tl+) possessing the trh gene but lacking the tdh gene (tdh−,trh+).
Figure 4:
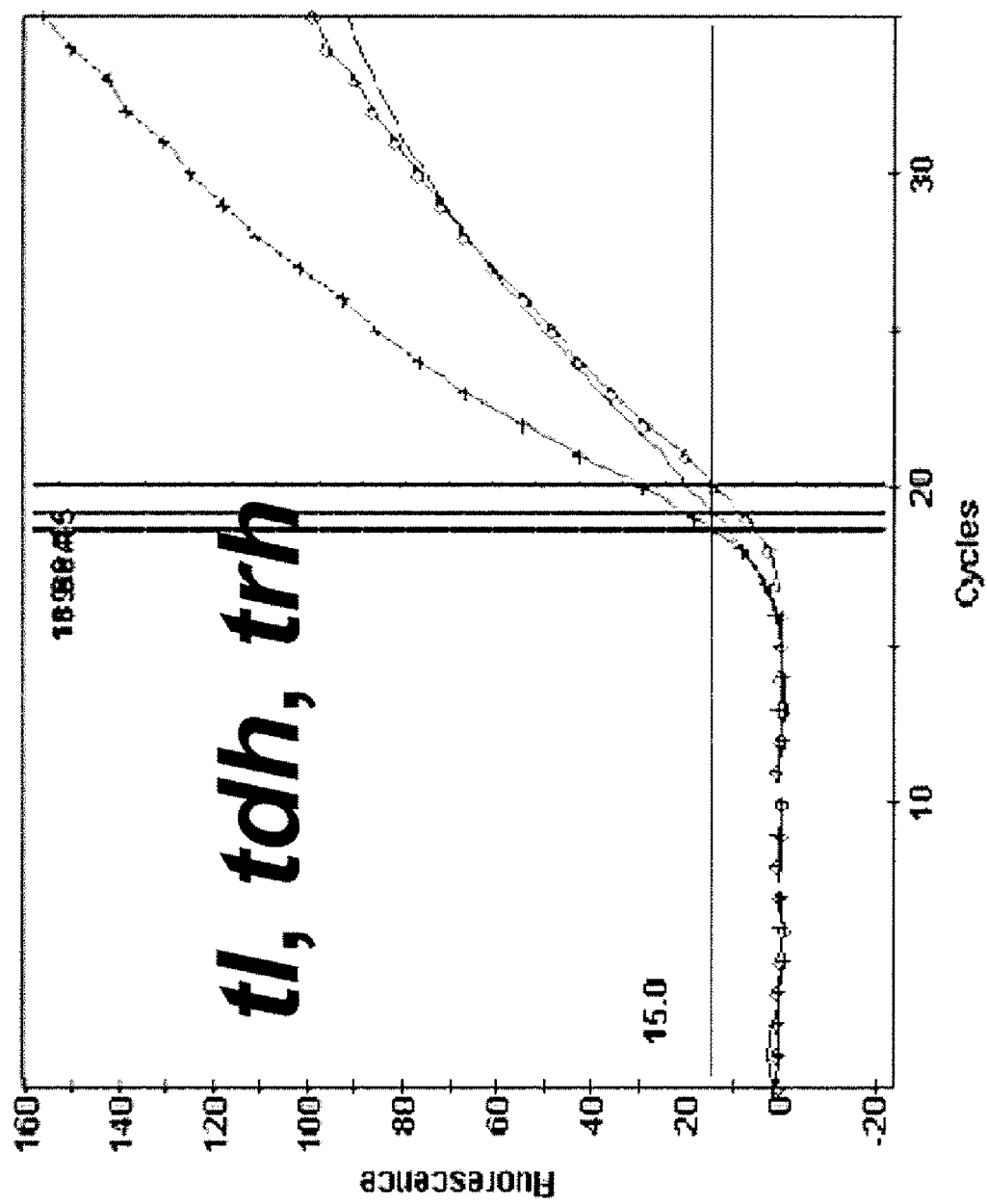
FIG. 4 illustrates a graph of cycles versus fluorescence showing multiplex amplification of tl, tdh, and trh from a Vp strain (tl+) possessing both the tdh gene and the trh gene (tdh+,trh+).

FIG. 1 depicts the results of the cycle threshold versus log fluorescence from the SMART® Cycler SC system. The results show multiplex amplification of the tl, tdh, and trh target genes (ROX™, FAM™, and TET™ channels respectively). FIG. 2 shows the cycle threshold versus log fluorescence for the multiplex amplification of the tl, tdh, and trh target genes from a Vp strain (tl+) possessing the tdh gene but lacking the trh gene (tdh+, trh−). Similarly, FIG. 3 shows the cycle threshold versus log fluorescence for the multiplex amplification of the tl, tdh, and trh target genes from a Vp strain (tl+) possessing the trh gene but lacking the tdh gene (tdh−, trh+). FIG. 4 shows the cycle threshold versus log fluorescence for the multiplex amplification of the tl, tdh, and trh target genes from a Vp strain (tl+) possessing both the trh gene and the tdh gene (tdh+, trh+). These figures show that the assay can amplify and detect Vp species having the various combinations of the pathogenic genes.

FIG. 5 depicts the cycle threshold versus log fluorescence of a multiplex amplification of the tl, tdh, and trh genes against a panel of diverse bacterial isolates (boiled cells). As seen there, none of the non-Vp isolates amplified or reported. The Vp pool tested in this run contained only isolates lacking the tdh and trh genes.

Figure 6:
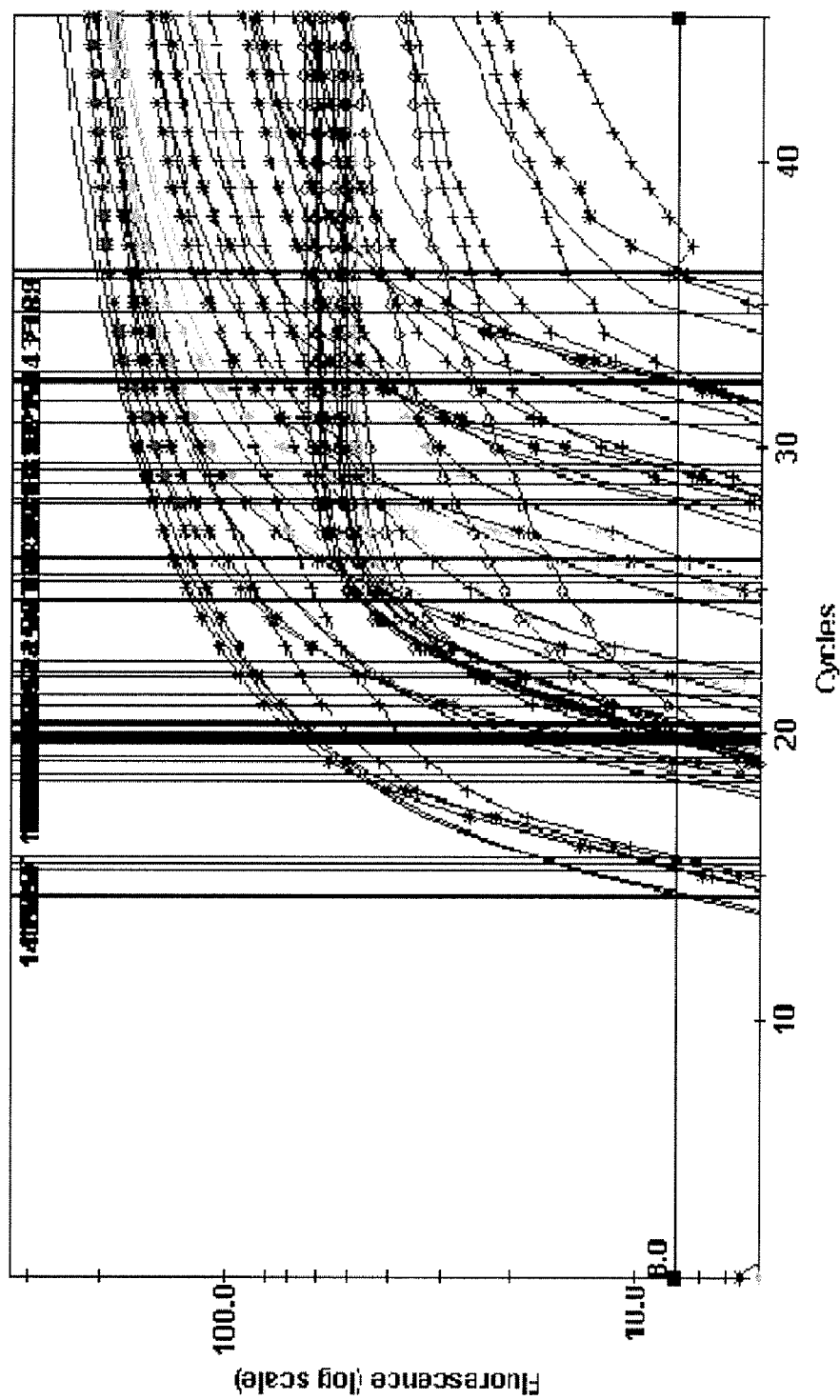
FIG. 6 illustrates plots of cycles versus fluorescence for multiplex amplification of 6-log template dilution range (2 replicates each) of the tl, tdh, and trh gene targets plus the internal control (TX-RED®, FAM™, TET™, and CY5® channels respectively).
Figure 7:
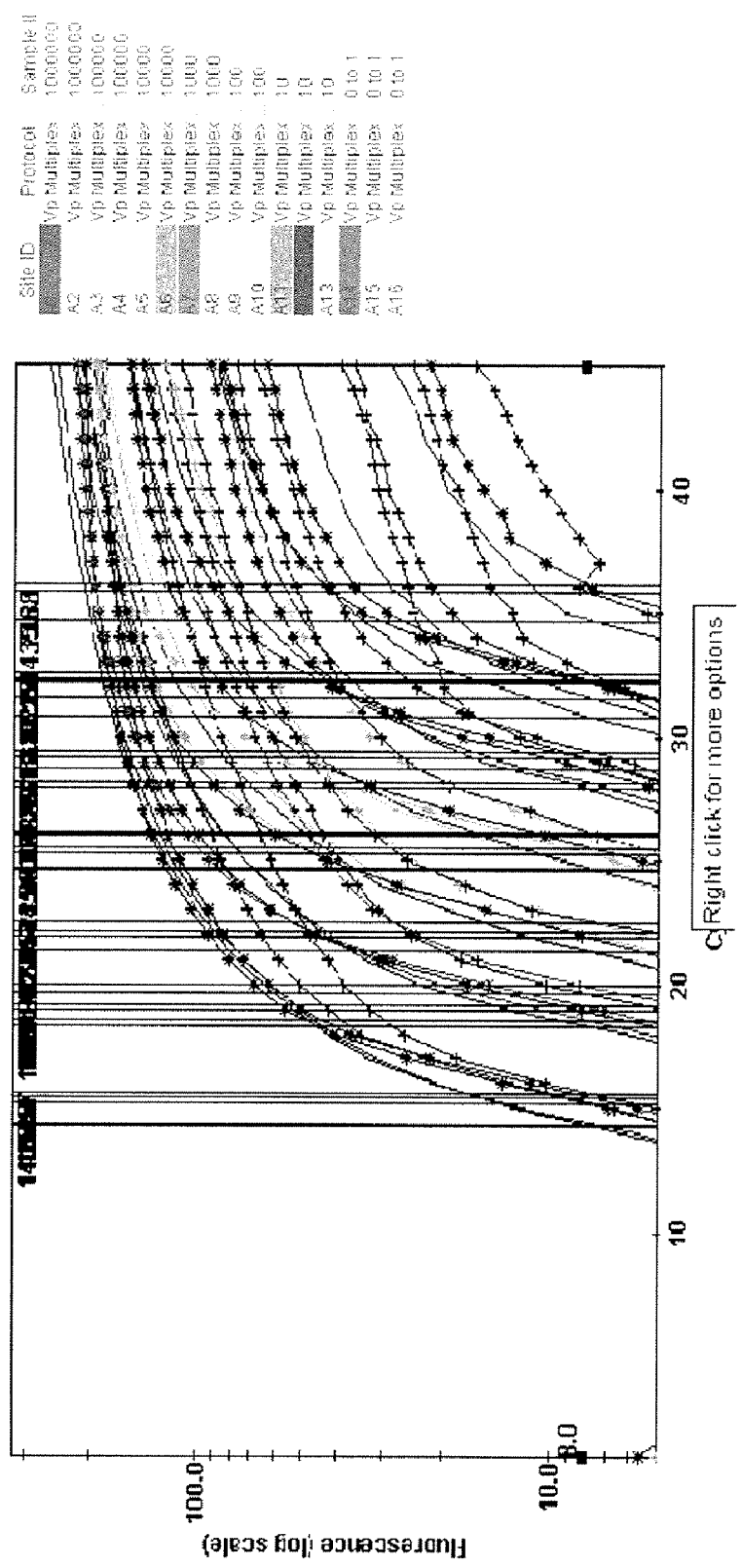
FIG. 7 illustrates the data of FIG. 6 with the internal control data removed.

FIG. 6 shows a 6-log template dilution range (two replicates each) for multiplex amplification of the tl, tdh, and trh gene targets plus the internal control TX-RED®, FAM™, TET™, and Cy-5® channels respectively). FIG. 7 shows the data of FIG. 6 with the internal control plot removed. As seen there, the assay has a dynamic range (>$10^6$ CFU equivalents to 1 CFU equivalent) and a cycle threshold value that is similar for each replicate at each dilution (i.e., the replicates are hard to distinguish).

Figure 8A:
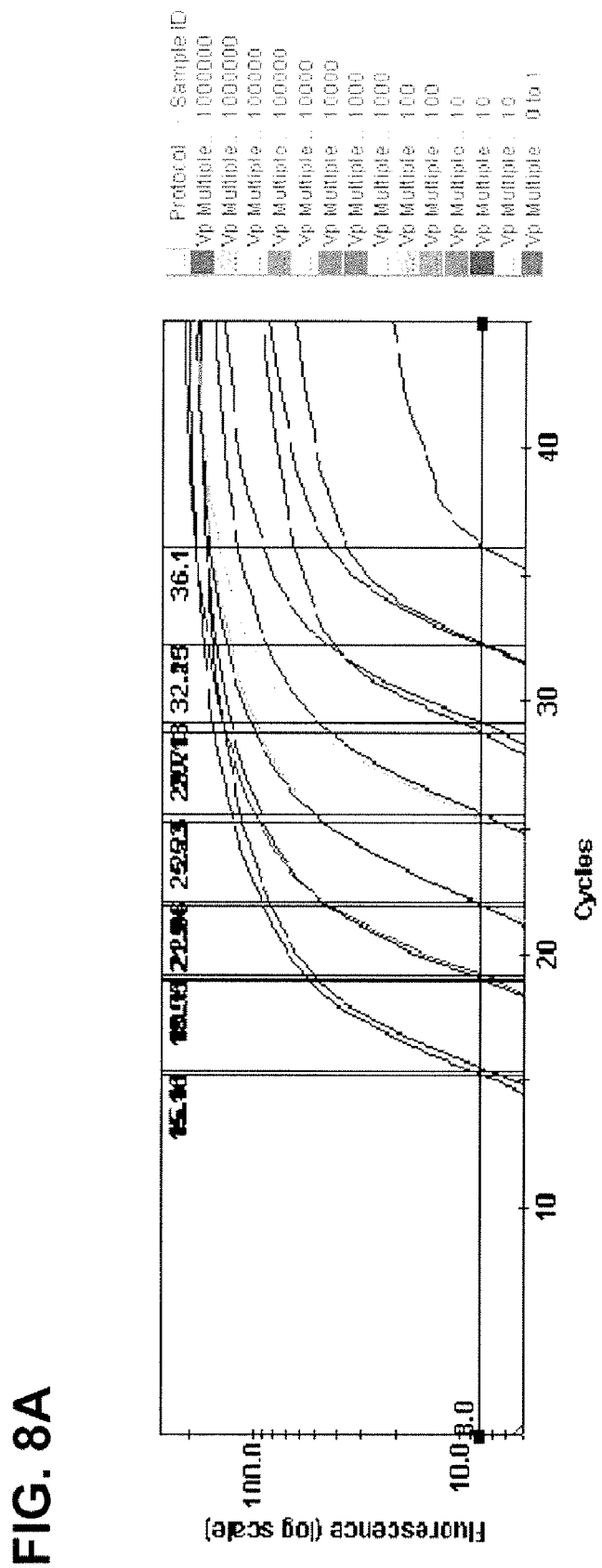
FIG. 8A illustrates the data for the tl gene from FIG. 6.
Figure 8B:
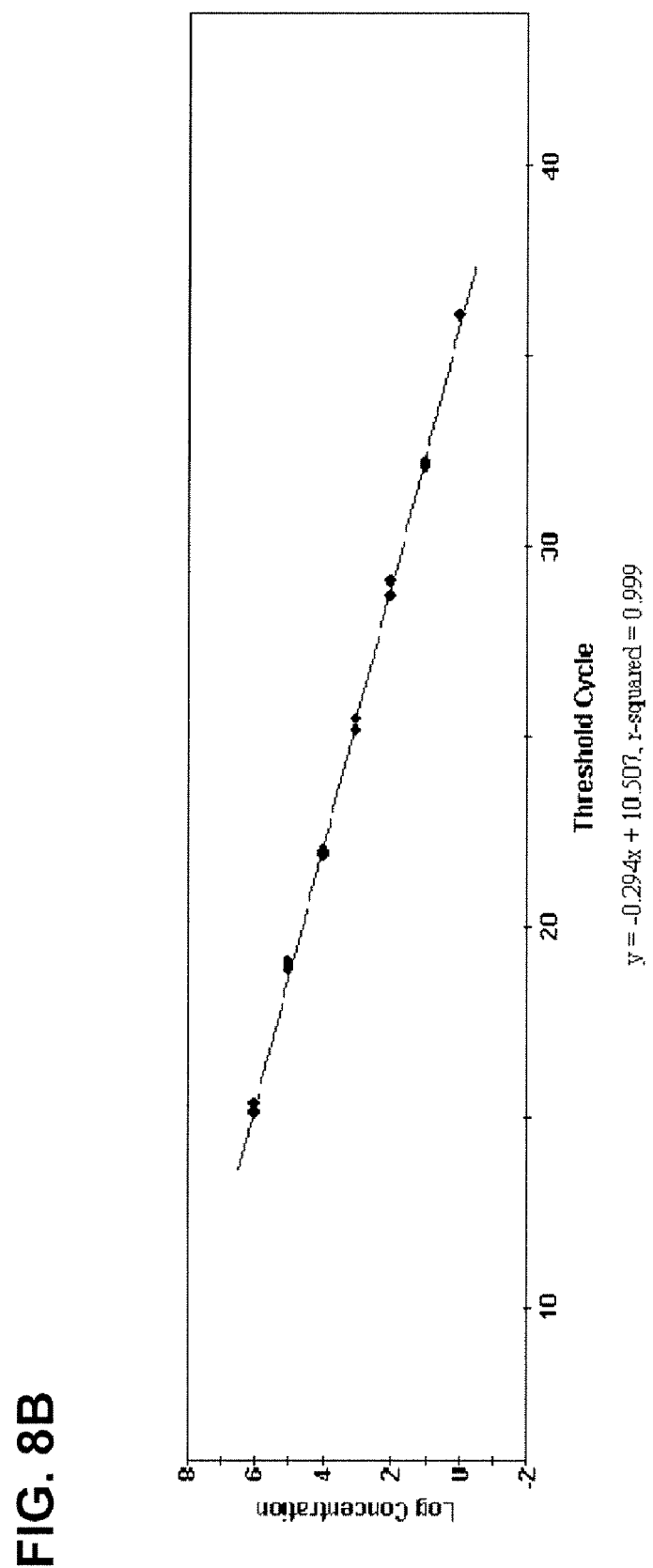
FIG. 8B illustrates a standard curve for the tl gene using the data from FIG. 8A.
Figure 9A:
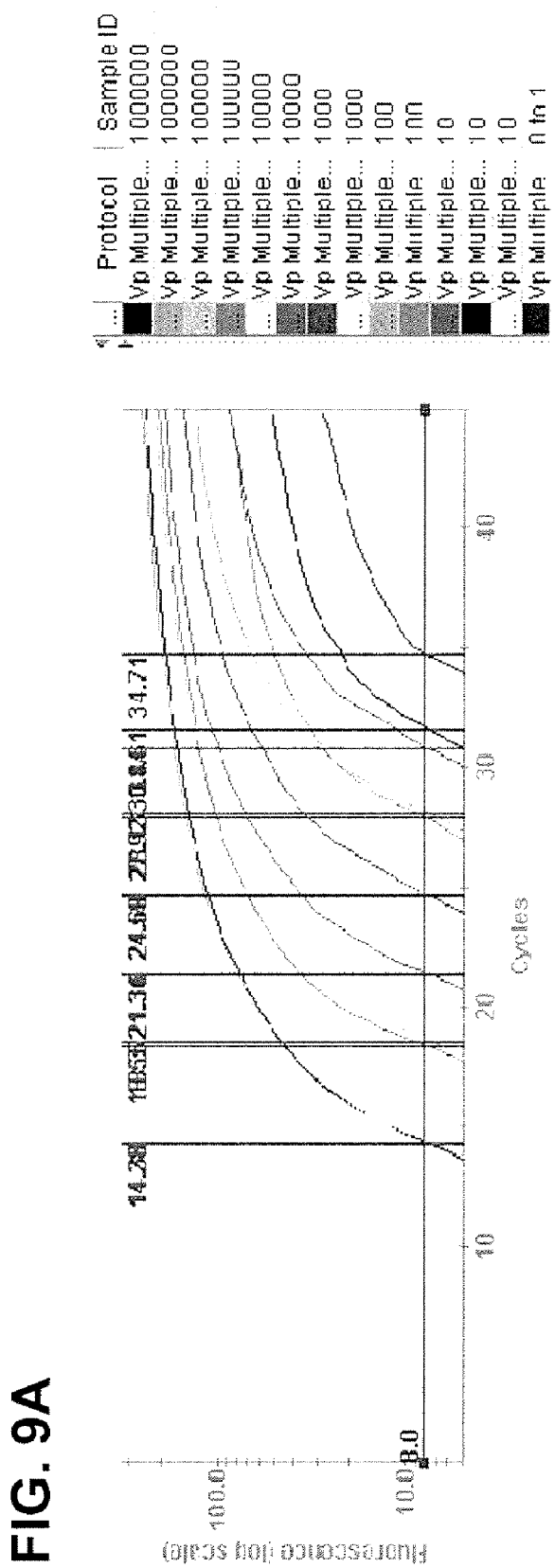
FIG. 9A illustrates the data for the tdh gene from FIG. 6.
Figure 9B:
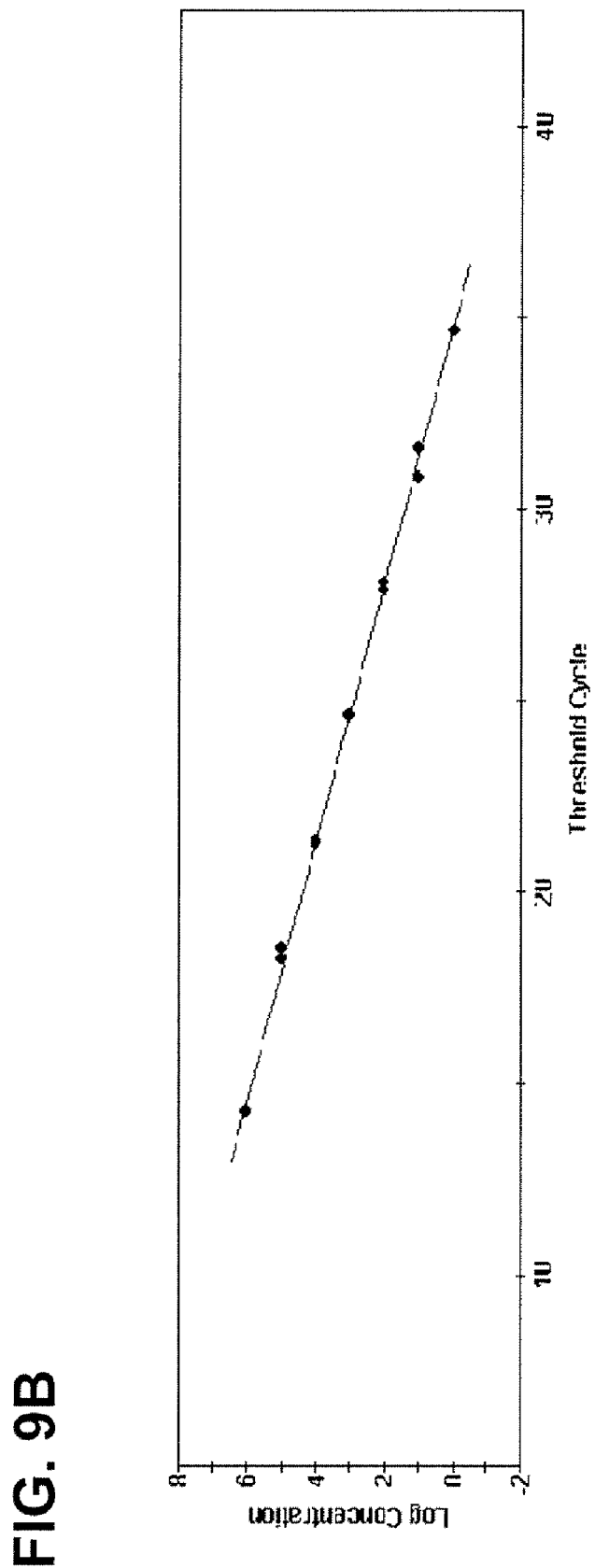
FIG. 9B illustrates a standard curve for the tdh gene using the data from FIG. 9A.
Figure 10A:
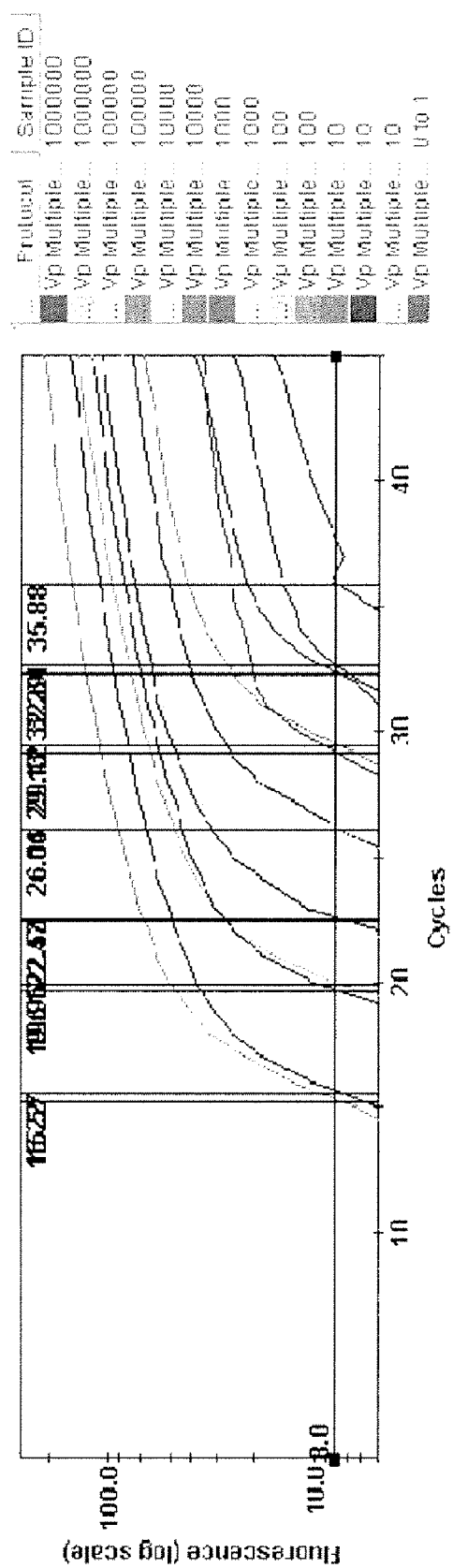
FIG. 10A illustrates the data for the trh gene from FIG. 6.
Figure 10B:
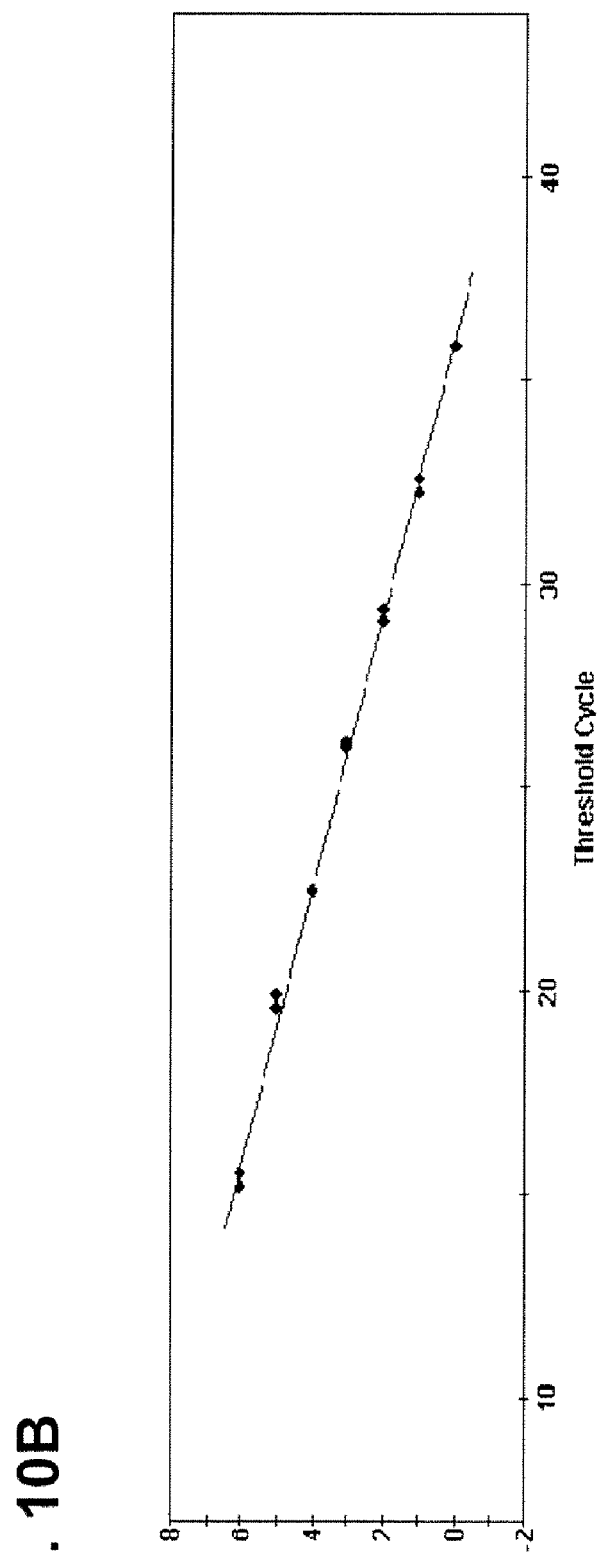
FIG. 10B illustrates a standard curve for the trh gene using the data from FIG. 10A.

FIG. 8A shows the data for the ti gene from FIG. 6. FIG. 8B shows a tl standard curve of cycle threshold versus log fluorescence for the data shown in FIG. 8A, along with a plot of the log cell number versus cycle threshold (the standard curve). As seen there, the correlation coefficient is 0.999, which is indicative of how well the data points fit the line. FIGS. 9A, 9B, and 10A and 10B show similar data and standard curves for the tdh and trh genes respectively. Those curves have correlation coefficients of 0.998 and 0.997 respectively.

Figure 11:
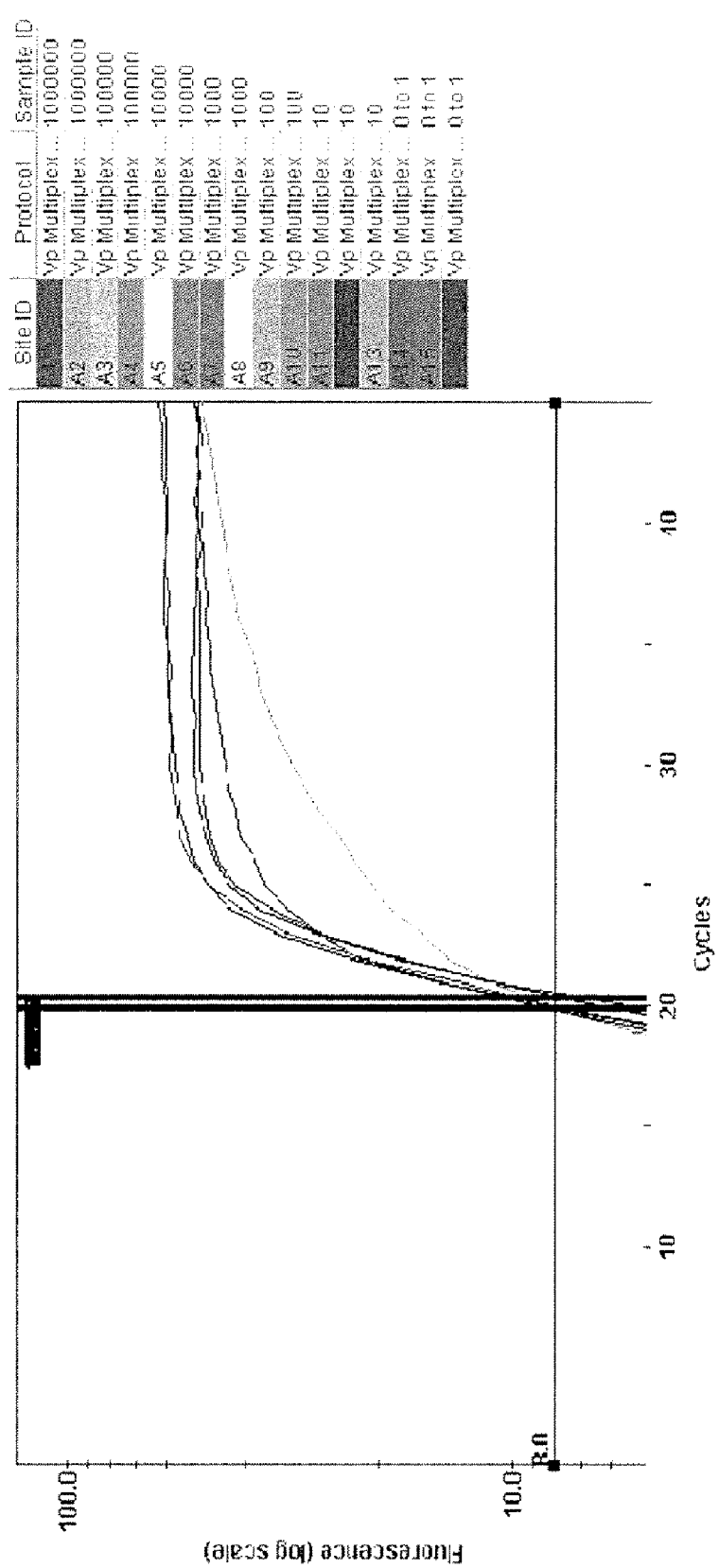
FIG. 11 illustrates cycles versus fluorescence for multiplex amplification of the internal control.

FIGS. 11A and 11B show the cycle threshold versus log fluorescence for the internal control data from FIG. 6. As can be seen there, the cycle threshold value for the internal control remains constant at about 20 cycles over the full dynamic range of the multiplex assay, during simultaneous quantification of the three target genes.

Figure 12A:
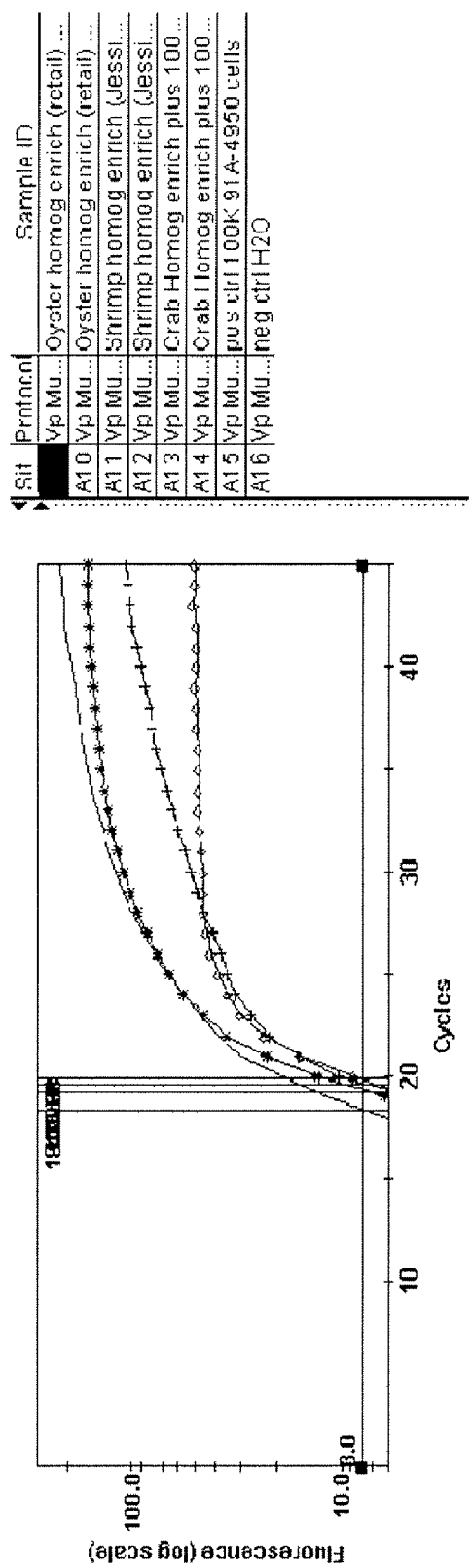
FIG. 12A illustrates cycles versus fluorescence for multiplex amplification of an oyster homogenate sample (1 µl) spiked with cells from a Vp strain possessing all three target genes and the internal control.
Figure 12B:
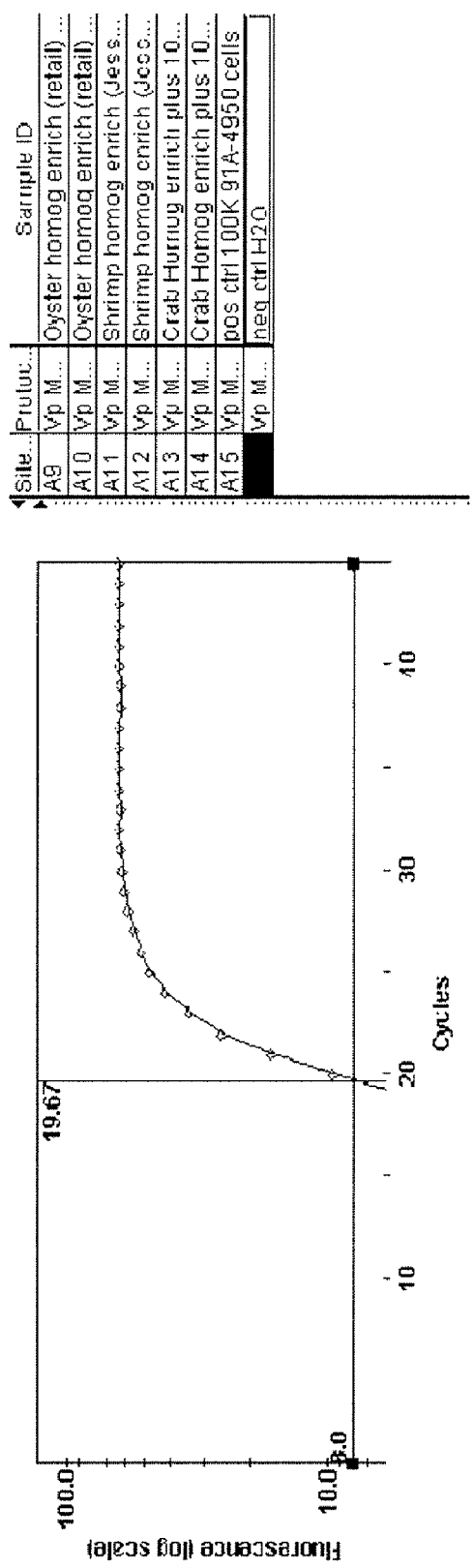
FIG. 12B illustrates cycles versus fluorescence for multiplex amplification of an oyster homogenate sample (1 µl) that was not spiked with cells from a Vp strain.
Figure 13A:
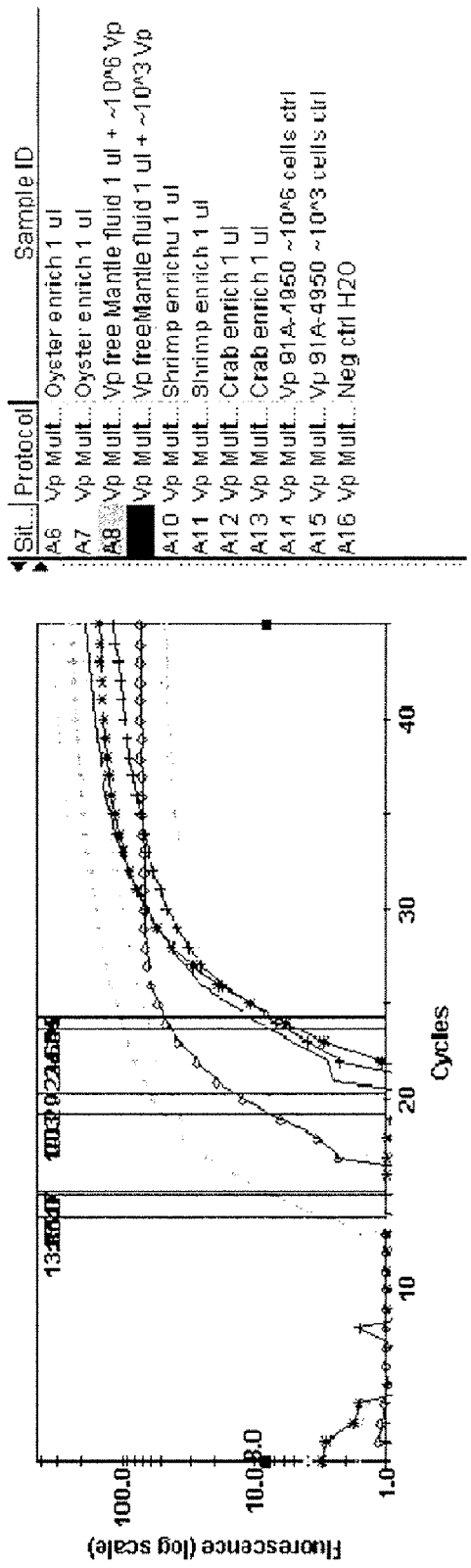
FIG. 13A illustrates cycles versus fluorescence for multiplex amplification of an oyster mantle fluid sample (1 µl) spiked with $10^3$ and $10^6$ cells from a Vp strain possessing all three target genes and the internal control.
Figure 13B:
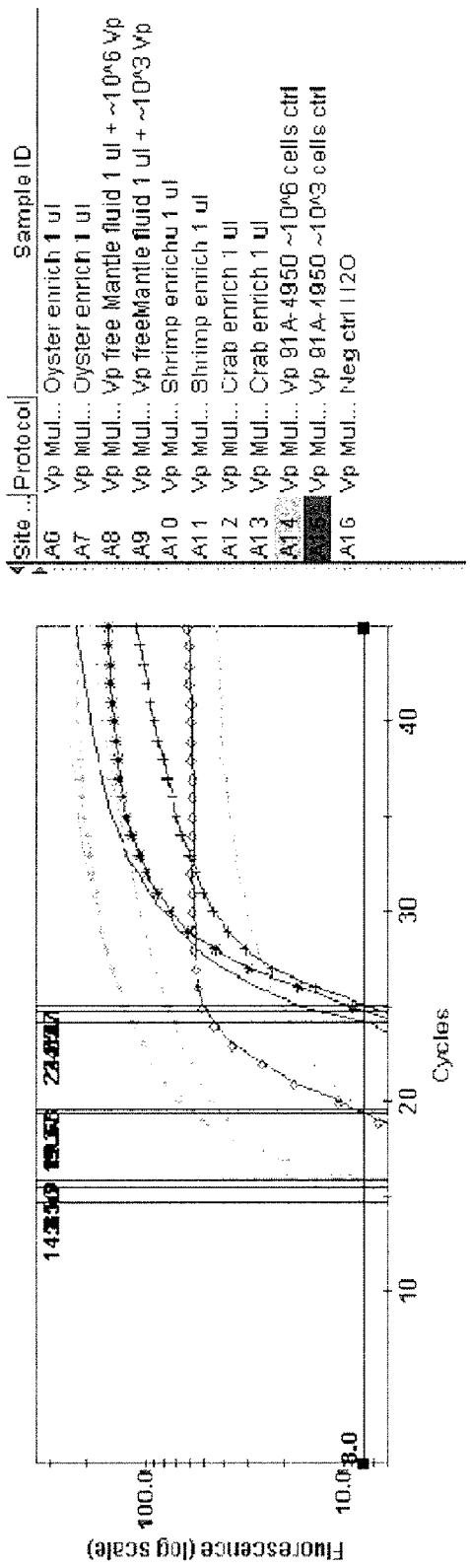
FIG. 13B illustrates cycles versus fluorescence for multiplex amplification of an oyster mantle fluid sample (1 µl) that was not spiked with cells from a Vp strain.
Figure 14A:
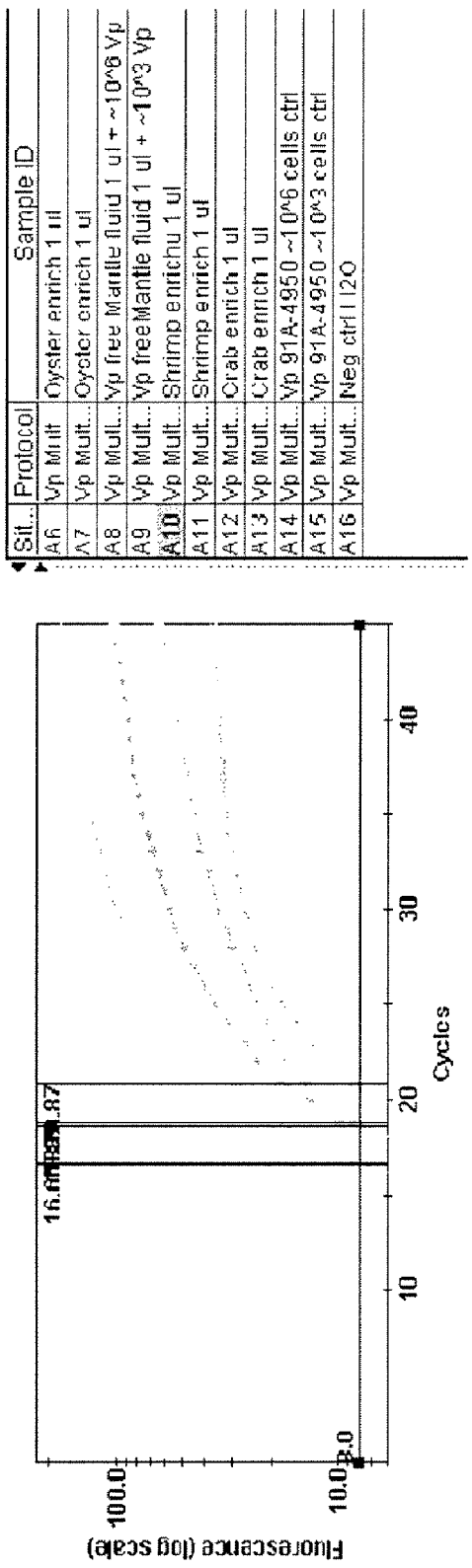
FIG. 14A illustrates cycles versus fluorescence for multiplex amplification of a shrimp homogenate sample (1 µl) spiked with cells from a Vp strain possessing all three target genes and the internal control.
Figure 14B:
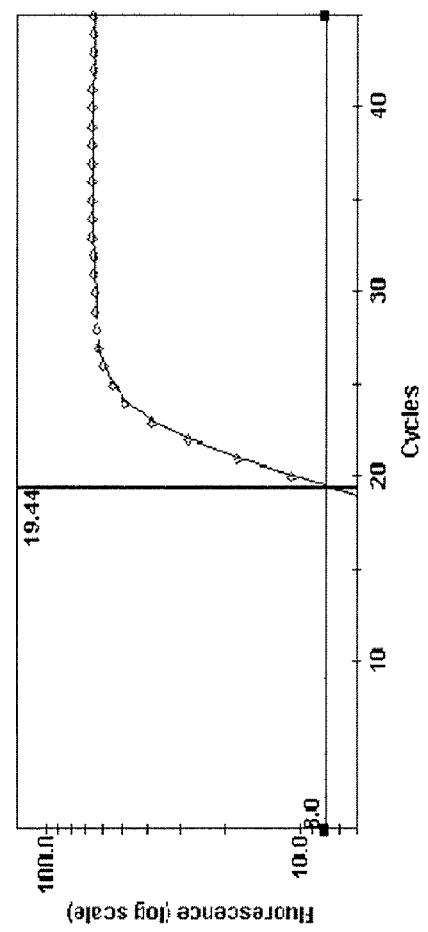
FIG. 14B illustrates cycles versus fluorescence for multiplex amplification of a shrimp homogenate sample (1 µl) that was not spiked with cells from a Vp strain.

FIG. 12A shows a plot cycle threshold versus log fluorescence for an oyster homogenate enrichment spiked with cells from a Vp strain possessing all three target genes. FIG. 12B is the same plot for the negative control (an oyster homogenate enrichment that was not spiked with cells from a Vp strain). The two plots show that the oyster enrichment (1 μL) did not significantly inhibit the PCR reaction because the internal control cycle threshold values were about the same for both. Similarly, FIGS. 13A and 13B show the same plots for Vp-free oyster mantle fluid (1 μL) spiked with $10^6$ and $10^3$ cells from a tdh+, trh+Vp strain, and a negative control. Again, the internal control cycle threshold values were approximately the same, indicating that the mantle fluid did not inhibit the reaction. FIGS. 14A and 14B present the same plots for shrimp homogenate samples, and again evidences no significant inhibition of the PCR reaction by no significant difference in the control cycle threshold values between the enriched sample and the negative control.

Conclusions

The assay was tested for specificity against a panel of greater than 100 strains representing thirteen different bacterial species. Only Vp strains possessing the appropriate target genes produced amplified target and generated fluorescent signal. The robustness of the assay was confirmed using a pure culture Vp template suspended in the following matrices: PBS, direct and concentrated oyster mantle fluid, oyster tissue enrichment, shrimp tissue enrichment, and crab tissue enrichment. The assay was shown to have a dynamic range of detection of >$10^6$ CFU to 1 CFU per reaction (with simultaneous detection of each target gene), and was demonstrated to be quantitative with a precision of detection within two-fold when tested using pure cultures of various Vp strains possessing tdh, trh, or both tdh and trh. Combining this real-time PCR assay with rapid and repeatable methods for sample and template preparation and concentration will allow same day direct enumeration of total and potentially virulent Vp from environmental sources and seafood.

The assay is highly specific for detection of the tl, tdh, and trh genes of *Vibrio parahaemolyticus*. Using pure cultures, the assay can simultaneously detect and quantify all 3 target genes with a high degree of accuracy, and has a 6-log dynamic range from >$10^6$ cells to a single CFU while quantifying all 3 targets simultaneously. The assay is capable of detection of Vp in oyster mantle fluid and seawater, and in enrichments of oyster homogenate, shrimp homogenate, crab homogenate, and other samples. The internal control utilized in this assay successfully prevented the reporting of false negatives, and may also be able to be used as a quantitative internal control to estimate PCR inhibition.

EXAMPLE 2

Other Examples of Internal Control Nucleic Acid Molecule Amplicons

Examples of primers utilized with the internal control nucleic acid molecule that were designed for use with temperature-limited internal control.

| Sequence: | TAGCCCTAAATCACCCTAC | SEQ ID NO:11 |
|---|---|---|
| Sequence: | AGCCATTCGTTACATTGTT | SEQ ID NO:12 |
| Sequence: | CGAGCAGTTTAGCCCTA | SEQ ID NO:13 |
| Sequence: | TTACATTGTTGAGGGCG | SEQ ID NO:14 |
| Sequence: | CAAGTTCATAATGACATCGAT | SEQ ID NO:15 |
| Sequence: | CCATTCGTTACATTGTTGA | SEQ ID NO:16 |
| Sequence: | CCGTTCGAGCAGTTTAG | SEQ ID NO:17 |
| Sequence: | GTACGACAATATTCGCGA | SEQ ID NO:18 |
| Sequence: | CAAGTTCATAATGACATCGA | SEQ ID NO:19 |
| Sequence: | CCATTCGTTACATTGTTG | SEQ ID NO:20 |
| Sequence: | TAGCCCTAAATCACCCTA | SEQ ID NO:21 |
| Sequence: | GCACAACAGCATCCAA | SEQ ID NO:22 |
| Sequence: | TAGCCCTAAATCACCCTAC | SEQ ID NO:23 |
| Sequence: | GCACAACAGCATCCAAT | SEQ ID NO:24 |

EXAMPLE 3

Use of Internal Control Molecules of Invention in Other Assays

Figure 15:
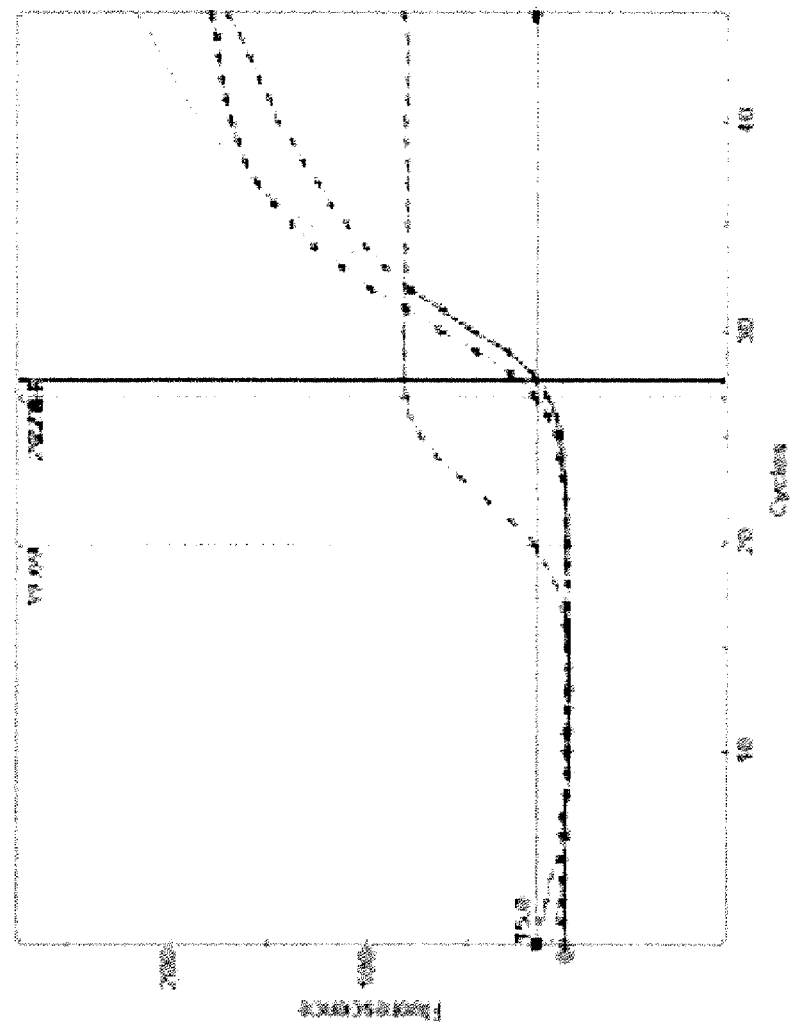
FIG. 15 illustrates cycles versus fluorescence for multiplex amplification of a sample having target genes and an internal control nucleic acid molecule in accordance with the invention.

FIG. 15 illustrates another use of an internal control nucleic acid molecule in accordance with the invention. This example was carried out in a fashion analogous to Example 1.

As seen there, the internal control molecule amplified with a cycle threshold (Ct) of about 20 cycles, indicating the absence of matrix inhibition in this example.

Figure 16:
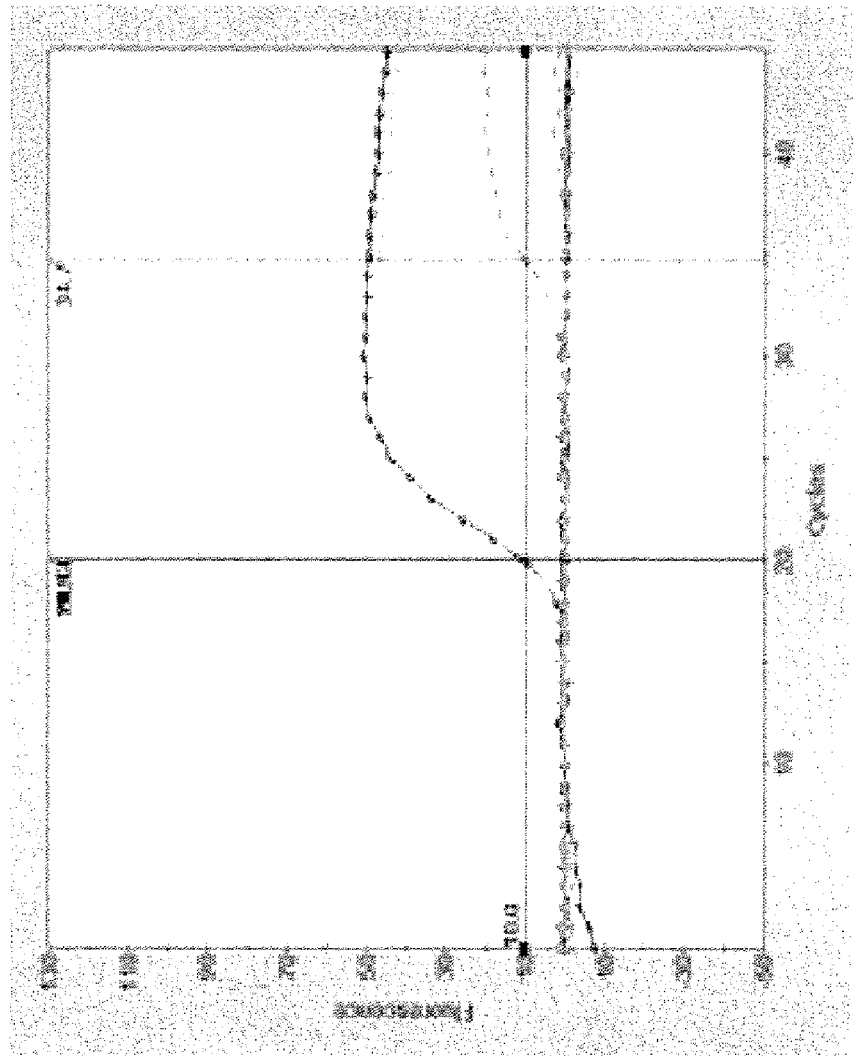
FIG. 16 illustrates cycles versus fluorescence for a cholera toxin gene assay that incorporated an internal control nucleic acid molecule of the invention.

FIG. 16 shows an internal control nucleic and molecule of the invention in an assay for the cholera toxin gene. As seen there, the internal control was inhibited by 15 PCR cycles, which indicated the presence of matrix inhibitors. The target gene did not amplify, but its presence or absence cannot be confirmed without further testing. The presence of the internal control showed that it was the matrix that was inhibiting the amplification, instead of simply leading to a report of a potentially false negative result.

Figure 17:
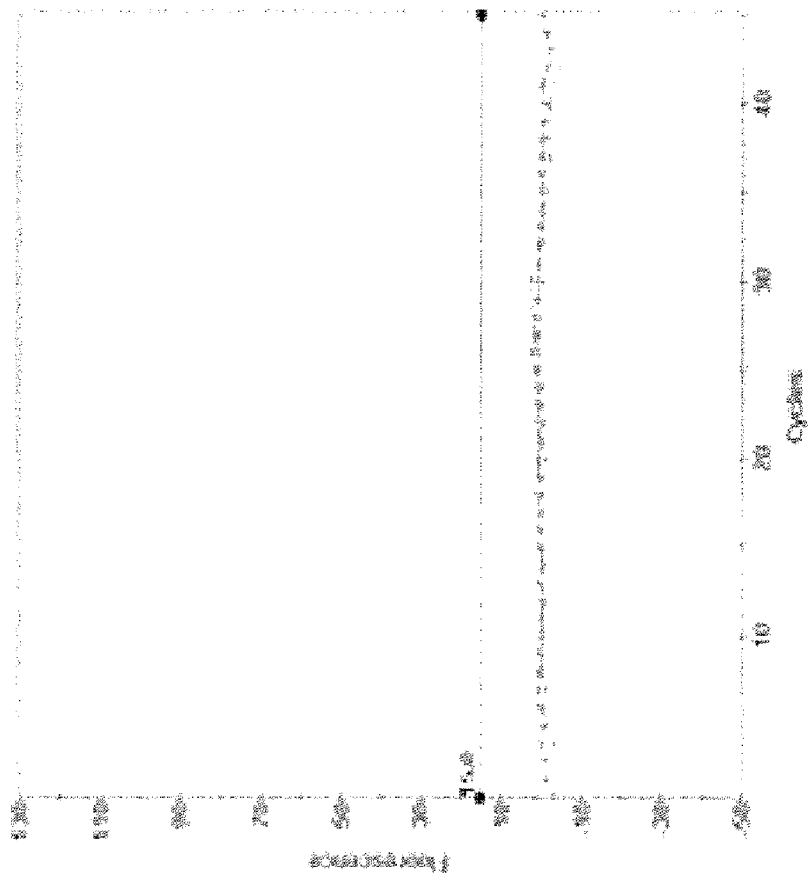
FIG. 17 illustrates cycles versus fluorescence for an ORF8 gene assay from a Vp strain that incorporated an internal control nucleic acid molecule of the invention.

FIG. 17 shows an internal control nucleic acid molecule in accordance with the invention in an assay for the ORF8 gene in Vp. As seen there, there was complete inhibition of amplification. Without the use of the internal control, a negative result would have been incorrectly reported.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. An internal control nucleic acid molecule comprising the sequence of SEQ ID NO:9.

2. A kit comprising:
   a) at least one internal control nucleic acid molecule according to claim 1 comprising: at least one forward primer binding site; at least one reverse primer binding site; and at least one amplifiable region;

wherein each of said forward primer binding site, said reverse primer binding site, and said amplifiable region are pseudo-randomly generated and lack identity to any known naturally occurring nucleic acid sequence or PCR-amplifiable region; and have sequences that do not have a string of more than four bases that are the same;

b) at least one forward primer, configured to be complementary to said at least one forward primer binding site of said internal control nucleic acid molecule, and having a sequence selected from the group consisting of SEQ ID NO:1, SEQ ID NO:2, SEQ ID NO:3, and combinations thereof; and c) at least one reverse primer, configured to be complementary to said at least one reverse primer binding site of said internal control nucleic acid molecule.

3. The kit of claim 2, wherein said kit comprises a plurality of internal control nucleic acid molecules.

4. The kit of claim 2, wherein said kit comprises a plurality of forward primers and a plurality of reverse primers.

5. The kit of claim 2, wherein said at least one reverse primer has a sequence chosen from the group consisting of: SEQ ID NO:4, SEQ ID NO:5, SEQ ID NO:6, SEQ ID NO:7, and SEQ ID NO:8.

6. The kit of claim 2, wherein said at least one internal control nucleic acid molecule comprises a probe binding site.

7. The kit according to claim 6, further comprising at least one probe.

8. The kit according to claim 7, wherein said probe has a sequence of SEQ ID NO:10.

9. The kit according to claim 7, wherein said probe is labeled.

10. The kit according to claim 2, wherein said internal control nucleic acid molecule is a linearized plasmid DNA molecule.

11. The kit according to claim 2, wherein said internal control nucleic acid molecule is a circular plasmid DNA molecule.

12. The kit according to claim 2, wherein said internal control nucleic acid molecule is a single stranded RNA molecule for use in RT-PCR.

13. The kit of claim 2, wherein said forward primer binding site and said reverse primer binding site of the internal control nucleic acid are each from about 15 to about 25 nucleic acids long.

14. The kit of claim 2, wherein said amplifiable region of the internal control nucleic acid molecule is from about 15 to about 1000 nucleic acids long.

15. The kit of claim 2, wherein each of said at least one forward primer binding site, said at least one reverse primer binding site, and said amplifiable region of the internal control nucleic acid have a specified range of GC content.

16. The kit of claim 2, wherein each of said at least one forward primer binding site, said at least one reverse primer binding site, and said amplifiable region of the internal control nucleic acid have sequences that do not have a string of more than five bases that are the same.

17. The kit of claim 4, wherein said plurality of forward primers and said plurality of reverse primers are chosen to anneal at different temperatures.

18. The kit of claim 4, wherein said plurality of forward primers and said plurality of reverse primers are chosen to provide an array of different sized amplifiable regions in said internal control nucleic acid molecule.

19. The kit of claim 9 wherein said probe is labeled with both a fluorophore and a quencher.

20. The kit of claim 19, wherein said fluorophore is a rhodamine, fluorescein, or cyanine fluorophore.

21. The kit of claim 19, wherein said quencher is a non-fluorescent quencher.

22. A kit comprising:
   a) at least one internal control nucleic acid molecule according to claim 1 comprising: at least one forward primer binding site; at least one reverse primer binding site; and at least one amplifiable region;

wherein each of said forward primer binding site, said reverse primer binding site, and said amplifiable region are pseudo-randomly generated and lack identity to any known naturally occurring nucleic acid sequence or PCR-amplifiable region; and have sequences that do not have a string of more than four bases that are the same;

b) at least one forward primer, configured to be complementary to said at least one forward primer binding site of said internal control nucleic acid molecule; and c) at least one reverse primer, configured to be complementary to said at least one reverse primer binding site of said internal control nucleic acid molecule, wherein said at least one reverse primer has a sequence chosen from the group consisting of: SEQ ID NO:4, SEQ ID NO:5, SEQ ID NO:6, SEQ ID NO:7, SEQ ID NO:8, and combinations thereof 23. The kit of claim 22, wherein said at least one forward primer has a sequence chosen from the group consisting of: SEQ ID NO:1, SEQ ID NO:2, SEQ ID NO:3, and combinations thereof.

24. The kit of claim 22, wherein said kit comprises a plurality of internal control nucleic acid molecules.

25. The kit of claim 22, wherein said kit comprises a plurality of forward primers and a plurality of reverse primers.

26. The kit of claim 22, wherein said at least one internal control nucleic acid molecule comprises a probe binding site.

27. The kit according to claim 26 further comprising at least one probe.

28. The kit according to claim 27, wherein said probe has a sequence of SEQ ID NO:10.

29. The kit according to claim 27, wherein said probe is labeled.

30. The kit of claim 22, wherein said forward primer binding site and said reverse primer binding site of the internal control nucleic acid are each from about 15 to about 25 nucleic acids long.

31. The kit of claim 22, wherein said amplifiable region of the internal control nucleic acid molecule is from about 15 to about 1000 nucleic acids long.

32. The kit of claim 25, wherein said plurality of forward primers and said plurality of reverse primers are chosen to anneal at different temperatures.

33. The kit of claim 25, wherein said plurality of forward primers and said plurality of reverse primers are chosen to provide an array of different sized amplifiable regions in said internal control nucleic acid molecule.

34. The internal control nucleic acid molecule of claim 1, further comprising a plurality of forward primer binding sites and a plurality of reverse primer binding sites.

35. The internal control nucleic acid molecule of claim 34, wherein said plurality of forward primer binding sites and said plurality of reverse primer binding sites are complementary to a plurality of forward primers and a plurality of reverse primers.

* * * * *